US011142533B2

(12) United States Patent
Rogers et al.

(10) Patent No.: US 11,142,533 B2
(45) Date of Patent: Oct. 12, 2021

(54) MACROCYCLES FOR USE IN TREATING DISEASE

(71) Applicant: TURNING POINT THERAPEUTICS, INC., San Diego, CA (US)

(72) Inventors: Evan W. Rogers, San Diego, CA (US); Jane Ung, San Diego, CA (US); Vivian Nguyen, San Diego, CA (US); Dayong Zhai, San Diego, CA (US); Wei Deng, San Diego, CA (US); Jingrong J. Cui, San Diego, CA (US)

(73) Assignee: Turning Point Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/214,096

(22) Filed: Mar. 26, 2021

(65) Prior Publication Data
US 2021/0246145 A1  Aug. 12, 2021

Related U.S. Application Data

(63) Continuation of application No. 17/110,051, filed on Dec. 2, 2020.

(60) Provisional application No. 63/015,937, filed on Apr. 27, 2020, provisional application No. 62/943,098, filed on Dec. 3, 2019.

(51) Int. Cl.
*C07D 498/22* (2006.01)
*A61P 35/00* (2006.01)

(52) U.S. Cl.
CPC ............ *C07D 498/22* (2013.01); *A61P 35/00* (2018.01)

(58) Field of Classification Search
CPC .............................. C07D 498/22; A61P 35/00
See application file for complete search history.

(56) References Cited

U.S. PATENT DOCUMENTS

| 9,370,519 | B2 | 6/2016 | Blom et al. |
| 2009/0274657 | A1 | 11/2009 | Gai et al. |
| 2017/0002023 | A1 | 1/2017 | Cui et al. |
| 2018/0186813 | A1 | 7/2018 | Cui et al. |

FOREIGN PATENT DOCUMENTS

WO         2019126122 A1    6/2019

OTHER PUBLICATIONS

Anastassiadis et al. (2011) "Comprehensive Assay of Kinase Catalytic Activity Reveals Features of Kinase Inhibitor Selectivity", Nature Biotechnology, 29(11):1039-1045 (19 pages).
Bagshawe Kenneth D. (1995) "Antibody-Directed Enzyme Prodrug Therapy: A Review", Drug Development Research, 34(2):220-230.
Berge et al. (1977) "Pharmaceutical Salts", Journal of Pharmaceutical Sciences, 66(1):1-19.
Bertolini et al. (1997) "A New Rational Hypothesis for the Pharmacophore of the Active Metabolite of Leflunomide, a Potent Immunosuppressive Drug", Journal of Medicinal Chemistry, 40(13):2011-2016.
Bischof et al. (Apr. 1997) "Role of the Nucleophosmin (NPM) Portion of the Non-Hodgkin's Lymphoma-Associated NPM-Anaplastic Lymphoma Kinase Fusion Protein in Oncogenesis", Molecular and Cellular Biology, 17(4):2312-2325.
Gainor et al. (Oct. 2016) "Molecular Mechanisms of Resistance to First- and Second-Generation ALK Inhibitors in ALK-Rearranged Lung Cancer", Cancer Discovery, 6(10):1118-1133.
Grande et al. (2011) "Targeting Oncogenic ALK: A Promising Strategy for Cancer Treatment", Molecular Cancer Therapeutics, 10:569-579.
Hallberg et al. (2013) "Mechanistic insight into ALK Receptor Tyrosine Kinase in Human Cancer Biology", Nature Reviews Cancer, 13(10):685-700.
Karuppaiah et al. (Mar. 18, 2016) "FGF Signaling in the Osteoprogenitor Lineage Non-Autonomously Regulates Postnatal Chondrocyte Proliferation and Skeletal Growth", The Company of Biologists Ltd., 143,1811-1822, 15 pages.
Katayama et al. (May 2015) "Therapeutic Targeting of Anaplastic Lymphoma Kinase in Lung Cancer: A Paradigm for Precision Cancer Medicine", Clinical Cancer Research, 21(10):2227-2235.
Malik et al. (2014) "U.S. Food and Drug Administration Approval: Crizotinib for Treatment of Advanced or Metastatic Non-Small Cell Lung Cancer That is Anaplastic Lymphoma Kinase Positive", Clinical Cancer Research, 20(8):2029-2034.
Manning et al. (Dec. 6, 2002) "The Protein Kinase Complement of the Human Genome", Science, 298(5600):1912-1934.
Morris et al. (1994) "Fusion of a Kinase Gene, ALK, to a Nucleolar Protein Gene, NPM, in Non-Hodgkin's Lymphoma", Science, 263(5151):1281-1284.
Mossé et al. (Oct. 16. 2008) "Identification of ALK as a Major Familial Neuroblastoma Predisposition Gene", Nature, 455(7215):930-935 (20 pages).
Ornitz et al. (Jul. 15, 2015) "Fibroblast Growth Factor Signaling in Skeletal Development and Disease", Genes & Development, Cold Spring Harbor Laboratory Press, 29(14): 1463-86, 24 pages.
Pulford et al. (2004) "The Emerging Normal and Disease-Related Roles of Anaplastic Lymphoma Kinase", Cellular and Molecular Life Sciences CMLS, 61(23):2939-2953.
Samsa et al. (Feb. 1, 2018) "Signaling Pathways Regulating Cartilage Growth Plate Formation and Activity", Semin Cell Dev Biol. Author manuscript, 30 pages.
Sawyers C. (Nov. 18, 2004) "Targeted Cancer Therapy". Nature, 432(7015):294-297.
Shan et al. (Jul. 1997) "Prodrug Strategies Based on Intramolecular Cyclization Reactions", Journal of Pharmaceutical Sciences, 86(7):765-767.
Shaw et al. (2019) "ALK Resistance Mutations and Efficacy of Lorlatinib in Advanced Anaplastic Lymphoma Kinase-Positive Non-Small-Cell Lung Cancer", Journal of Clinical Oncology, 37(16):1370-1379.
Soda et al. (Aug. 2, 2007) "Identification of the Transforming EML4-ALK Fusion Gene in Non-small-cell Lung Cancer", Nature, 448(7153):561-566.

(Continued)

*Primary Examiner* — John M Mauro
(74) *Attorney, Agent, or Firm* — Mintz, Levin, Cohn, Ferris, Glovsky and Popeo, P.C.

(57) ABSTRACT

The present disclosure relates to certain chiral diaryl macrocyclic derivatives, pharmaceutical compositions containing them, and methods of using them to treat cancer.

3 Claims, 5 Drawing Sheets

(56) References Cited

OTHER PUBLICATIONS

Xie et al. (2014) "Recent Research on the Growth Plate: Advances in Fibroblast Growth Factor Signaling in Growth Plate Development and Disorders", Bioscientifica Ltd., Journal of Molecular Endocrinology, 53(1):T11-34, 24 pages.
Yoda et al. (Jun. 2018) "Sequential ALK Inhibitors Can Select for Lorlatinib-Resistant Compound ALK Mutations in ALK-Positive Lung Cancer", Cancer Discovery, 8(6):714-729.
International Search Report and Written Opinion received for PCT Application No. PCT/US2020/062859, dated Feb. 11, 2021, 8 pages.

MACROCYCLES FOR USE IN TREATING DISEASE

CROSS REFERENCES TO RELATED APPLICATIONS

This application is a continuation application of U.S. application Ser. No. 17/110,511 filed Dec. 2, 2020, which claims priority to U.S. Provisional Application No. 62/943,098 filed Dec. 3, 2019; and U.S. Provisional Application No. 63/015,937 filed Apr. 27, 2020, the disclosures of each of which are incorporated by reference in their entireties.

TECHNICAL FIELD

The present disclosure relates to certain diaryl macrocyclic derivatives, pharmaceutical compositions containing them, and methods of using them to treat cancer.

BACKGROUND

Protein kinases are key regulators for cell growth, proliferation and survival. Genetic and epigenetic alterations accumulate in cancer cells leading to abnormal activation of signal transduction pathways which drive malignant processes. Manning, G. et al., *Science* 2002, 298, 1912-1934. Pharmacological inhibition of these signaling pathways presents promising intervention opportunities for targeted cancer therapies. Sawyers, C., *Nature* 2004, 432, 294-297.

Anaplastic lymphoma kinase (ALK), along with leukocyte tyrosine kinase (LTK), is grouped within the insulin receptor (IR) superfamily of receptor tyrosine kinases. ALK is mainly expressed in the central and peripheral nervous systems suggesting a potential role in normal development and function of the nervous system. Pulford, K. et al., *Cell Mol. Life Sci.* 2004, 61, 2939. ALK was first discovered as a fusion protein, NPM (nucleophosmin)-ALK, encoded by a fusion gene arising from the t(2;5)(p23;q35) chromosomal translocation in anaplastic large cell lymphoma (ALCL) cell lines. Morris, S. W. et al., *Science* 1994, 263, 1281. More than twenty distinct ALK translocation partners have been discovered in many cancers, including ALCL (60-90% incidence), inflammatory myofibroblastic tumors (IMT, 50-60%), non-small cell lung carcinomas (NSCLC, 3-7%), colorectal cancers (CRC, 0-2.4%), breast cancers (0-2.4%), and other carcinomas. Grande, E. et al., *Mol. Cancer Ther.* 2011, 10, 569-579. The ALK-fusion proteins are located in the cytoplasm, and the fusion partners with ALK play a role in dimerization or oligomerization of the fusion proteins through a coil-coil interaction to generate constitutive activation of ALK kinase function. Bischof, D. et al., *Mol. Cell Biol.*, 1997, 17, 2312-2325. EML4-ALK, which comprises portions of the echinoderm microtubule associated protein-like 4 (EML4) gene and the ALK gene, was first discovered in NSCLC, is highly oncogenic, and was shown to cause lung adenocarcinoma in transgenic mice. Soda, M. et al., *Nature* 2007, 448, 561-566. Oncogenic point mutations of ALK occur in both familial and sporadic cases of neuroblastoma. Mosse, Y. P. et al., *Nature* 2008, 455, 930-935. ALK is an attractive molecular target for cancer therapeutic intervention because of the important roles in haematopoietic, solid, and mesenchymal tumors. Grande, supra.

Since the first discovery of NPM (nucleophosmin)-ALK fusion gene in anaplastic large cell lymphoma cell lines in 1994 (Morris S W, et al *Science.* 1994; 263(5151):1281-4), alterations of ALK have been found in a wide range of cancer types, including anaplastic large cell lymphoma, inflammatory myofibroblastic tumor, diffuse large B cell lymphoma, NSCLC, renal medulla carcinoma, renal cell carcinoma, breast cancer, colon carcinoma, serous ovarian carcinoma, and esophageal squamous cell carcinoma (Hallberg B, et al *Nat Rev Cancer.* 2013; 13(10):685-700). The clinical benefit of targeting oncogenic ALK fusions over chemotherapy in ALK+ NSCLC patients has led to a full regular approval of crizotinib (Malik S M, et al *Clin Cancer Res.* 2014; 20(8):2029-34). However, resistance to crizotinib treatment occurred within an average of 7.3-10.9 months. The resistance mechanisms include ALK gene amplification, acquired mutations in the kinase domain, bypass signaling, EMT, and CNS metastasis (Katayama R, et al *Clin Cancer Res.* 2015; 21(10):2227-35). Although the more potent second generation ALK inhibitors ceritinib, alectinib and brigatinib can initially effectively overcome crizotinib resistance, patients ultimately relapse on these inhibitors as well. Analysis of post-progression biopsy specimens indicated that each ALK inhibitor is associated with a distinct spectrum of ALK resistance mutations and ALK G1202R is a common resistance mutation to the first and second generations of ALK inhibitors (Gainor J F, et al Cancer Discov. 2016 October; 6(10):1118-1133). The solvent front mutations, including ALK G1202R, G1202del, D1203N, S1206Y/C, and E1210K increase significantly after second generation ALK inhibitor treatment, especially brigatinib having up to 71% solvent front mutations in 7 biopsied resistant patients (Gainor J F, et al Cancer Discov. 2016 October; 6(10):1118-1133).

The current treatment paradigm for patients with ALK+ cancer is to treat them with sequential ALK targeted therapies. The third-generation ALK inhibitor lorlatinib has demonstrated clinical activity in patients who failed previous ALK inhibitors and was approved for ALK positive metastatic NSCLC patients after crizotinib and at least one other ALK inhibitor treatment (Shaw A, et al *J. Clin Oncol* 2019, 37:1370-1379). However, Compound mutations emerge as a new challenge after more than one ALK TKI treatment. Seven of 20 samples (35%) harbored compound ALK mutations after lorlatinib treatment, e. g. lorlatinib is no longer active against compound gatekeeper and solvent front mutations ALK L1196M/G1202R (Yoda S., et al *Cancer Discovery* 2018, 8(6):714-729).

Endochondral ossification is a process that results in both the replacement of the embryonic cartilaginous skeleton during organogenesis and the growth of long bones until adult height is achieved. Fibroblast growth factor (FGF)/FGF receptor (FGFR) signaling plays a vital role in the development and maintenance of growth plates in endochondral ossification process (Xie Y 2014). Missense mutations in FGFs and FGFRs can cause multiple genetic skeletal diseases with disordered endochondral ossification. Activating mutations in FGFR3 cause achondroplasia, the most common form of dwarfism among live births (Samsa WE 2017). The growth plates of humans with FGFR3 mutations show disrupted chondrocyte columns and reduced numbers of hypertrophic chondrocytes. FGFR1 and FGFR2 play many essential and mostly redundant roles during development, including growth plate formation. FGFR2-deficient embryos fail to form limb buds (Ornitz DM 2015). In addition, Overexpression of FGFR1 in chondrocytes causes joint fusion. Deletion of both FGFR1 and FGFR2 in mice caused a decreased length of the growth plate with a reduced number of proliferating chondrocytes (Karuppaiah K 2016). Therefore, the selectivity over FGFRs is an important parameter for better safety profile, especially for pediatric population.

Therefore, there is a new demand to develop next generation ALK inhibitors that show potent activity against a broad spectrum of resistant mutations, especially solvent front mutations, such as ALK G1202R, and compounds mutations, such as ALK L1196M/G1202R. Furthermore, there is a demand for such ALK inhibitors to show selectivity over FGFRs. Certain chiral diaryl macrocyclic compounds have been found in the context of this disclosure to have this advantageous activity profile.

SUMMARY

In one aspect, the disclosure relates to a compound of the formula

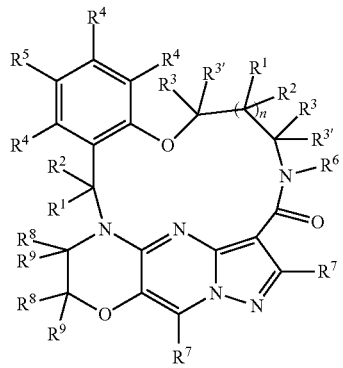

I wherein
each $R^1$ and $R^2$ is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, —$OR^a$, —$OC(O)R^a$, —$OC(O)R^a$, —$OC(O)NR^aR^b$, —$OS(O)R^a$, —$OS(O)_2R^a$, —$SR^a$, —$S(O)R^a$, —$S(O)_2R^a$, —$S(O)NR^aR^b$, —$S(O)_2NR^aR^b$, —$OS(O)NR^aR^b$, —$OS(O)_2NR^aR^b$, —$NR^aR^b$, —$NR^aC(O)R^b$, —$NR^aC(O)OR^b$, —$NR^aC(O)NR^aR^b$, —$NR^aS(O)R^b$, —$NR^aS(O)_2R^b$, —$NR^aS(O)NR^aR^b$, —$NR^aS(O)_2NR^aR^b$, —$C(O)R^a$, —$C(O)OR^a$, —$C(O)NR^aR^b$, —$PR^aR^b$, —$P(O)R^aR^b$, —$P(O)_2R^aR^b$, —$P(O)NR^aR^b$, —$P(O)_2NR^aR^b$, —$P(O)OR^a$, —$P(O)_2OR^a$, —CN, or —$NO_2$; or $R^1$ and $R^2$ taken together with the carbon atom to which they are attached combine to form a $C_3$-$C_6$ cycloalkyl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, and mono- or bicyclic heteroaryl is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS (O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

each $R^3$ and $R^{3'}$ is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, —$OR^a$, —$OC(O)R^a$, —$OC(O)R^a$, —$OC(O)NR^aR^b$, —$OS(O)R^a$, —$OS(O)_2R^a$, —$SR^a$, —$S(O)R^a$, —$S(O)_2R^a$, —$S(O)NR^aR^b$, —$S(O)_2NR^aR^b$, —$OS(O)NR^aR^b$, —$OS(O)_2NR^aR^b$, —$NR^aR^b$, —$NR^aC(O)R^b$, —$NR^aC(O)OR^b$, —$NR^aC(O)NR^aR^b$, —$NR^aS(O)R^b$, —$NR^aS(O)_2R^b$, —$NR^aS(O)NR^aR^b$, —$NR^aS(O)_2NR^aR^b$, —$C(O)R^a$, —$C(O)OR^a$, —$C(O)NR^aR^b$, —$PR^aR^b$, —$P(O)R^aR^b$, —$P(O)_2R^aR^b$, —$P(O)NR^aR^b$, —$P(O)_2NR^aR^b$, —$P(O)OR^a$, —$P(O)_2OR^a$, —CN, or —$NO_2$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$; or $R^3$ and $R^{3'}$ taken together with the carbon atom to which they are attached combine to form a $C_3$-$C_6$ cycloalkyl; wherein each hydrogen atom in $C_3$-$C_6$ cycloalkyl is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$; or both $R^{3'}$ taken together combine to form a divalent group —$(CR^1R^2)_m$—;

each $R^4$ and $R^5$ is independently hydrogen, deuterium, halogen, —OW, —$OC(O)R^c$, —$OC(O)NR^cR^d$, —$OC(=N)NR^cR^d$, —$OS(O)R^c$, —$OS(O)_2R^c$, —$OS(O)NR^cR^d$, —$OS(O)_2NR^cR^d$, —$SR^c$, —$S(O)R^c$, —$S(O)_2R^c$, —$S(O)NR^cR^d$, —$S(O)_2NR^cR^d$, —$NR^cR^d$, —$NR^cC(O)R^d$, —$NR^cC(O)OR^d$, —$NR^cC(O)NR^cR^d$, —$NR^cC(=N)NR^cR^d$, —$NR^cS(O)R^d$, —$NR^cS(O)_2R^d$, —$NR^cS(O)NR^cR^d$, —$NR^cS(O)_2NR^cR^d$, —$C(O)R^c$, —$C(O)OR^c$, —$C(O)NR^cR^d$, —$C(=N)NR^cR^d$, —$PR^cR^d$, —$P(O)R^cR^d$, —$P(O)_2R^cR^d$, —$P(O)NR^cR^d$, —$P(O)_2NR^cR^d$, —$P(O)OR$, —$P(O)_2OR^c$, —CN, —$NO_2$, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, $C_5$-$C_8$ cycloalkyl, or 5- to 8-membered heterocycloalkyl is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

$R^6$ is H, deuterium, or $C_1$-$C_6$ alkyl, wherein each hydrogen atom in $C_1$-$C_6$ alkyl is independently optionally substituted by deuterium, halogen, —$OR^e$, —$SR^e$, or —$NR^eR^f$;

each $R^7$ is independently hydrogen or deuterium;

each $R^8$ and $R^9$ is independently H, deuterium, halogen, —CN, —$OR^e$, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, or alternatively, R⁸ and R⁹ taken together with the carbon to which they are attached form a $C_3$-$C_6$ cycloalkyl or a 4- to 6-membered heterocycloalkyl, or alternatively, R⁸ and R⁹ taken together with the carbon to which they are attached form an exocyclic ethylene group, wherein each hydrogen atom in $C_1$-$C_6$ alkyl, $C_2$-$C_6$ alkenyl, $C_2$-$C_6$ alkynyl, $C_3$-$C_6$ cycloalkyl, 4- to 6-membered heterocycloalkyl, 3- to 7-membered heterocycloalkyl, $C_6$-$C_{10}$ aryl, exocyclic ethylene group, or mono- or bicyclic heteroaryl is optionally substituted by a halogen, —N3, —CN, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, or —P(O)$_2$OR$^e$;

each R$^a$, R$^b$, R$^e$, R$^d$, R$^e$, and R$^f$ is independently selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, and 5- to 7-membered heteroaryl;

m is 1 or 2; and n is 0, 1, 2, or 3;

or a pharmaceutically acceptable salt thereof.

In another aspect, the disclosure relates to a compound of the formula

I wherein each R¹ and R² is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, —OR$^a$, —OC(O)R$^a$, —OC(O)R$^a$, —OC(O)NR$^a$R$^b$, —OS(O)R$^a$, —OS(O)$_2$R$^a$, —SR$^a$, —S(O)R$^a$, —S(O)$_2$R$^a$, —S(O)NR$^a$R$^b$, —S(O)$_2$NR$^a$R$^b$, —OS(O)NR$^a$R$^b$, —OS(O)$_2$NR$^a$R$^b$, —NR$^a$R$^b$, —NR$^a$C(O)R$^b$, —NR$^a$C(O)OR$^b$, —NR$^a$C(O)NR$^a$R$^b$, —NR$^a$S(O)R$^b$, —NR$^a$S(O)$_2$R$^b$, —NR$^a$S(O)NR$^a$R$^b$, —NR$^a$S(O)$_2$NR$^a$R$^b$, —C(O)R$^a$, —C(O)OR$^a$, —C(O)NR$^a$R$^b$, —PR$^a$R$^b$, —P(O)R$^a$R$^b$, —P(O)$_2$R$^a$R$^b$, —P(O)NR$^a$R$^b$, —P(O)$_2$NR$^a$R$^b$, —P(O)OR$^a$, —P(O)$_2$OR$^a$, —CN, or —NO$_2$; or R¹ and R² taken together with the carbon atom to which they are attached combine to form a $C_3$-$C_6$ cycloalkyl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, and mono- or bicyclic heteroaryl is independently optionally substituted by deuterium, halogen, $C_1$-$C_6$ alkyl, $C_1$-$C_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$;

each R³ and R³' is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, —OR$^a$, —OC(O)R$^a$, —OC(O)R$^a$, —OC(O)NR$^a$R$^b$, —OS(O)R$^a$, —OS(O)$_2$R$^a$, —SR$^a$, —S(O)R$^a$, —S(O)$_2$R$^a$, —S(O)NR$^a$R$^b$, —S(O)$_2$NR$^a$R$^b$, —OS(O)NR$^a$R$^b$, —OS(O)$_2$NR$^a$R$^b$, —NR$^a$R$^b$, —NR$^a$C(O)R$^b$, —NR$^a$C(O)OR$^b$, —NR$^a$C(O)NR$^a$R$^b$, —NR$^a$S(O)R$^b$, —NR$^a$S(O)$_2$R$^b$, —NR$^a$S(O)NR$^a$R$^b$, —NR$^a$S(O)$_2$NR$^a$R$^b$, —C(O)R$^a$, —C(O)OR$^a$, —C(O)NR$^a$R$^b$, —PR$^a$R$^b$, —P(O)R$^a$R$^b$, —P(O)$_2$R$^a$R$^b$, —P(O)NR$^a$R$^b$, —P(O)$_2$NR$^a$R$^b$, —P(O)OR$^a$, —P(O)$_2$OR$^a$, —CN, or —NO$_2$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, is independently optionally substituted by deuterium, halogen, $C_1$-$C_6$ alkyl, $C_1$-$C_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$; or R³ and R³' taken together with the carbon atom to which they are attached combine to form a $C_3$-$C_6$ cycloalkyl; wherein each hydrogen atom in $C_3$-$C_6$ cycloalkyl is independently optionally substituted by deuterium, halogen, $C_1$-$C_6$ alkyl, $C_1$-$C_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$;

each R⁴ and R⁵ is independently hydrogen, deuterium, halogen, —OW, —OC(O)R$^c$, —OC(O)NR$^c$R$^d$, —OC(=N)NR$^c$R$^d$, —OS(O)R$^c$, —OS(O)$_2$R$^c$, —OS(O)NR$^c$R$^d$, —OS(O)$_2$NR$^c$R$^d$, —SR$^c$, —S(O)R$^c$, —S(O)$_2$R$^c$, —S(O)NR$^c$R$^d$, —S(O)$_2$NR$^c$R$^d$, —NR$^c$R$^d$, —NR$^c$C(O)R$^d$, —NR$^c$C(O)OR$^d$, —NR$^c$C(O)NR$^c$R$^d$, —NR$^c$C(=N)NR$^c$R$^d$, —NR$^c$S(O)R$^d$, —NR$^c$S(O)$_2$R$^d$, —NR$^c$S(O)NR$^c$R$^d$, —NR$^c$S(O)$_2$NR$^c$R$^d$, —C(O)R$^c$, —C(O)OR$^c$, —C(O)NR$^c$R$^d$, —C(=N)NR$^c$R$^d$, —PR$^c$R$^d$, —P(O)R$^c$R$^d$, —P(O)$_2$R$^c$R$^d$, —P(O)NR$^c$R$^d$, —P(O)$_2$NR$^c$R$^d$, —P(O)OR, —P(O)$_2$OR$^c$, —CN, —NO$_2$, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, $C_5$-$C_8$ cycloalkyl, or 5- to 8-membered heterocycloalkyl is independently optionally substituted by deuterium, halogen, $C_1$-$C_6$ alkyl, $C_1$-$C_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$;

R$^6$ is H, deuterium, or C$_1$-C$_6$ alkyl, wherein each hydrogen atom in C$_1$-C$_6$ alkyl is independently optionally substituted by deuterium, halogen, —OR$^e$, —SR$^e$, or —NR$^e$R$^f$;

each R$^7$ is independently hydrogen or deuterium;

each R$^a$, R$^b$, R$^c$, R$^d$, R$^e$, and R$^f$ is independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, and 5- to 7-membered heteroaryl; and n is 0, 1, 2, or 3;

or a pharmaceutically acceptable salt thereof.

In an aspect of the compound of formula I or a pharmaceutically acceptable salt thereof:

each R$^1$ and R$^2$ is independently H or C$_1$-C$_6$ alkyl;

each R$^3$ and R$^{3'}$ is independently H or C$_1$-C$_6$ alkyl; or R$^3$ and R$^{3'}$ taken together with the carbon atom to which they are attached combine to form a C$_3$-C$_6$ cycloalkyl;

each R$^4$ and R$^5$ is independently hydrogen or halogen;

R$^6$ is H or C$_1$-C$_6$ alkyl;

each R$^7$ is hydrogen; and n is 0 or 1.

In an aspect of the compound of formula I or a pharmaceutically acceptable salt thereof:

each R$^1$ and R$^2$ is independently H or C$_1$-C$_3$ alkyl;

each R$^3$ and R$^{3'}$ is independently H or C$_1$-C$_3$ alkyl; or R$^3$ and R$^{3'}$ taken together with the carbon atom to which they are attached combine to form a C$_3$-C$_4$ cycloalkyl;

each R$^4$ and R$^5$ is independently hydrogen or halogen;

R$^6$ is H;

each R$^7$ is hydrogen; and n is 0 or 1.

In an aspect of the compound of formula I or a pharmaceutically acceptable salt thereof:

each R$^1$ and R$^2$ is independently hydrogen or methyl;

each R$^3$ and R$^{3'}$ is independently hydrogen or methyl; or R$^3$ and R$^{3'}$ taken together with the carbon atom to which they are attached combine to form a cyclopropyl;

each R$^4$ and R$^5$ is independently hydrogen or fluorine;

R$^6$ is hydrogen;

each R$^7$ is hydrogen; and n is 0 or 1.

In an aspect of the compound of formula I, or a pharmaceutically acceptable salt thereof, has the structure of formula II, IIa, III, or IIIa.

In another aspect, the disclosure relates to a compound of the formula II or a pharmaceutically acceptable salt thereof.

In another aspect, the disclosure relates to a compound of the formula IIa or a pharmaceutically acceptable salt thereof.

In another aspect, the disclosure relates to a compound of the formula III or a pharmaceutically acceptable salt thereof.

In another aspect, the disclosure relates to a compound of the formula IIIa or a pharmaceutically acceptable salt thereof.

In another aspect, the disclosure provides a pharmaceutical composition comprising a compound of any one of the disclosed aspects, or a pharmaceutically acceptable salt thereof, and optionally at least one diluent, carrier or excipient.

In another aspect, the disclosure provides a method of treating cancer comprising administering to a subject in need of such treatment an effective amount of at least one compound of any one of the disclosed aspects, or a pharmaceutically acceptable salt thereof.

In another aspect, the disclosure provides a use of a compound of any one of the disclosed aspects, or a pharmaceutically acceptable salt thereof, in the preparation of a medicament for the treatment of cancer.

In another aspect, the disclosure provides a use of a compound of any one of the disclosed aspects, or a pharmaceutically acceptable salt thereof, for treating cancer.

In another aspect, the disclosure provides a compound of the disclosed aspects, or a pharmaceutically acceptable salt thereof, for use in treating cancer in a subject.

In another aspect, the disclosure provides a method of inhibiting ALK receptor tyrosine kinase, comprising contacting a cell comprising one or more of such kinases with an effective amount of at least one compound of any one of the disclosed aspects, or a pharmaceutically acceptable salt thereof, and/or with at least one pharmaceutical composition of the disclosure, wherein the contacting is in vitro, ex vivo, or in vivo.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A compound of the formula I

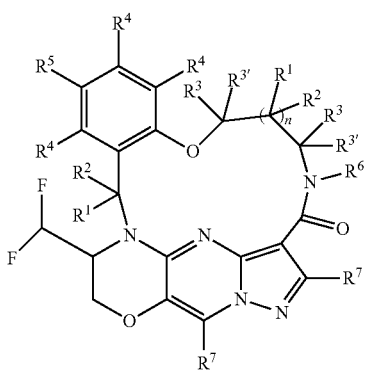

wherein
each $R^1$ and $R^2$ is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, —$OR^a$, —$OC(O)R^a$, —$OC(O)R^a$, —$OC(O)NR^aR^b$, —$OS(O)R^a$, —$OS(O)_2R^a$, —$SR^a$, —$S(O)R^a$, —$S(O)_2R^a$, —$S(O)NR^aR^b$, —$S(O)_2NR^aR^b$, —$OS(O)NR^aR^b$, —$OS(O)_2NR^aR^b$, —$NR^aR^b$, —$NR^aC(O)R^b$, —$NR^aC(O)OR^b$, —$NR^aC(O)NR^aR^b$, —$NR^aS(O)R^b$, —$NR^aS(O)_2R^b$, —$NR^aS(O)NR^aR^b$, —$NR^aS(O)_2NR^aR^b$, —$C(O)R^a$, —$C(O)OR^a$, —$C(O)NR^aR^b$, —$PR^aR^b$, —$P(O)R^aR^b$, —$P(O)_2R^aR^b$, —$P(O)NR^aR^b$, —$P(O)_2NR^aR^b$, —$P(O)OR^a$, —$P(O)_2OR^a$, —CN, or —$NO_2$; or $R^1$ and $R^2$ taken together with the carbon atom to which they are attached combine to form a $C_3$-$C_6$ cycloalkyl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, and mono- or bicyclic heteroaryl is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

each $R^3$ and $R^{3'}$ is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, —$OR^a$, —$OC(O)R^a$, —$OC(O)R^a$, —$OC(O)NR^aR^b$, —$OS(O)R^a$, —$OS(O)_2R^a$, —$SR^a$, —$S(O)R^a$, —$S(O)_2R^a$, —$S(O)NR^aR^b$, —$S(O)_2NR^aR^b$, —$OS(O)NR^aR^b$, —$OS(O)_2NR^aR^b$, —$NR^aR^b$, —$NR^aC(O)R^b$, —$NR^aC(O)OR^b$, —$NR^aC(O)NR^aR^b$, —$NR^aS(O)R^b$, —$NR^aS(O)_2R^b$, —$NR^aS(O)NR^aR^b$, —$NR^aS(O)_2NR^aR^b$, —$C(O)R^a$, —$C(O)OR^a$, —$C(O)NR^aR^b$, —$PR^aR^b$, —$P(O)R^aR^b$, —$P(O)_2R^aR^b$, —$P(O)NR^aR^b$, —$P(O)_2NR^aR^b$, —$P(O)OR^a$, —$P(O)_2OR^a$, —CN, or —$NO_2$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$; or $R^3$ and $R^{3'}$ taken together with the carbon atom to which they are attached combine to form a $C_3$-$C_6$ cycloalkyl; wherein each hydrogen atom in $C_3$-$C_6$ cycloalkyl is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(=N)NR^eR^f$, —$OS(O)R^e$, —$OS(O)_2R^e$, —$OS(O)NR^eR^f$, —$OS(O)_2NR^eR^f$, —$SR^e$, —$S(O)R^e$, —$S(O)_2R^e$, —$S(O)NR^eR^f$, —$S(O)_2NR^eR^f$, —$NR^eR^f$, —$NR^eC(O)R^f$, —$NR^eC(O)OR^f$, —$NR^eC(O)NR^eR^f$, —$NR^eS(O)R^f$, —$NR^eS(O)_2R^f$, —$NR^eS(O)NR^eR^f$, —$NR^eS(O)_2NR^eR^f$, —$C(O)R^e$, —$C(O)OR^e$, —$C(O)NR^eR^f$, —$PR^eR^f$, —$P(O)R^eR^f$, —$P(O)_2R^eR^f$, —$P(O)NR^eR^f$, —$P(O)_2NR^eR^f$, —$P(O)OR^e$, —$P(O)_2OR^e$, —CN, or —$NO_2$;

each $R^4$ and $R^5$ is independently hydrogen, deuterium, halogen, —$OR^c$, —$OC(O)R^c$, —$OC(O)NR^cR^d$, —$OC(=N)NR^cR^d$, —$OS(O)R^c$, —$OS(O)_2R^c$, —$OS(O)NR^cR^d$, —$OS(O)_2NR^cR^d$, —$SR^c$, —$S(O)R^c$, —$S(O)_2R^c$, —$S(O)NR^cR^d$, —$S(O)_2NR^cR^d$, —$NR^cR^d$, —$NR^cC(O)R^d$, —$NR^cC(O)OR^d$, —$NR^cC(O)NR^cR^d$, —$NR^cC(=N)NR^cR^d$, —$NR^cS(O)R^d$, —$NR^cS(O)_2R^d$, —$NR^cS(O)NR^cR^d$, —$NR^cS(O)_2NR^cR^d$, —$C(O)R^c$, —$C(O)OR^c$, —$C(O)NR^cR^d$, —$C(=N)NR^cR^d$, —$PR^cR^d$, —$P(O)R^cR^d$, —$P(O)_2R^cR^d$, —$P(O)NR^cR^d$, —P(O)₂NRᶜRᵈ, —P(O)OR, —P(O)₂ORᶜ, —CN, —NO₂, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, or mono- or bicyclic heteroaryl, wherein each hydrogen atom in C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, mono- or bicyclic heteroaryl, C₅-C₈ cycloalkyl, or 5- to 8-membered heterocycloalkyl is independently optionally substituted by deuterium, halogen, C₁-C₆ alkyl, C₁-C₆ haloalkyl, —ORᵉ, —OC(O)Rᵉ, —OC(O)NRᵉRᶠ, —OC(=N)NRᵉRᶠ, —OS(O)Rᵉ, —OS(O)₂Rᵉ, —OS(O)NRᵉRᶠ, —OS(O)₂NRᵉRᶠ, —SRᵉ, —S(O)Rᵉ, —S(O)₂Rᵉ, —S(O)NRᵉRᶠ, —S(O)₂NRᵉRᶠ, —NRᵉRᶠ, —NRᵉC(O)Rᶠ, —NRᵉC(O)ORᶠ, —NRᵉC(O)NRᵉRᶠ, —NRᵉS(O)Rᶠ, —NRᵉS(O)₂Rᶠ, —NRᵉS(O)NRᵉRᶠ, —NRᵉS(O)₂NRᵉRᶠ, —C(O)Rᵉ, —C(O)ORᵉ, —C(O)NRᵉRᶠ, —PRᵉRᶠ, —P(O)RᵉRᶠ, —P(O)RᵉRᶠ, —P(O)NRᵉRᶠ, —P(O)₂NRᵉRᶠ, —P(O)ORᵉ, —P(O)₂ORᵉ, —CN, or —NO₂;

R⁶ is H, deuterium, or C₁-C₆ alkyl, wherein each hydrogen atom in C₁-C₆ alkyl is independently optionally substituted by deuterium, halogen, —ORᵉ, —SRᵉ, or —NRᵉRᶠ;

each R⁷ is independently hydrogen or deuterium;

each Rᵃ, Rᵇ, 12', Rᵈ, Rᵉ, and Rᶠ is independently selected from the group consisting of H, deuterium, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, and 5- to 7-membered heteroaryl; and n is 0, 1, 2, or 3;

or a pharmaceutically acceptable salt thereof.

2. The compound of clause 1, or a pharmaceutically acceptable salt thereof, wherein n is 0 or 1.

3. The compound of clause 1 or 2, or a pharmaceutically acceptable salt thereof, wherein n is 0.

4. The compound of clause 1 or 2, or a pharmaceutically acceptable salt thereof, wherein n is 1.

5. The compound of any one of clauses 1 to 3, having the formula II

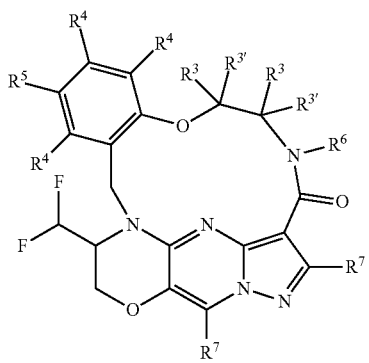

or a pharmaceutically acceptable salt thereof.

6. The compound of any one of clauses 1 to 3, or 5, having the formula IIa

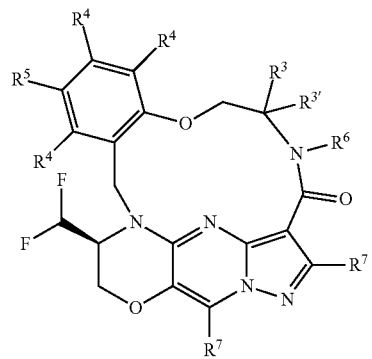

or a pharmaceutically acceptable salt thereof.

7. The compound of any one of clauses 1, 2, or 4, having the formula III

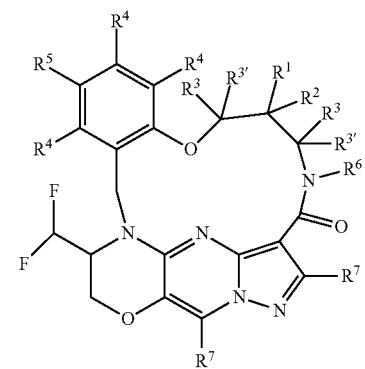

or a pharmaceutically acceptable salt thereof.

8. The compound of any one of clauses 1, 2, 4, or 7, having the formula IIIa

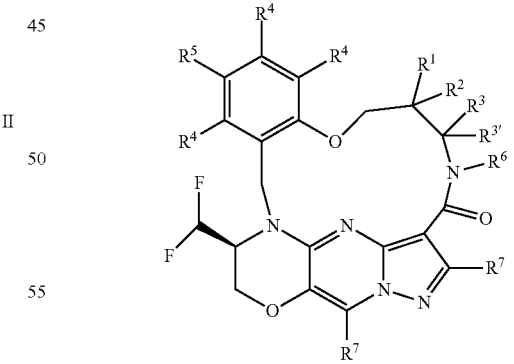

or a pharmaceutically acceptable salt thereof.

9. The compound of any one of the preceding clauses, or a pharmaceutically acceptable salt thereof, wherein each R¹ and R², when present, is independently H, deuterium, C₁-C₆ alkyl, or R¹ and R² taken together with the carbon atom to which they are attached combine to form a C₃-C₆ cycloalkyl.

10. The compound of any one of the preceding clauses, or a pharmaceutically acceptable salt thereof, wherein each R³ and R³' is independently H, deuterium, C₁-C₆ alkyl, or R³ and R³' taken together with the carbon atom to which they are attached combine to form a C₃-C₆ cycloalkyl.

11. The compound of any one of the preceding clauses, or a pharmaceutically acceptable salt thereof, wherein each R³' is H or deuterium.

12. The compound of any one of the preceding clauses, or a pharmaceutically acceptable salt thereof, wherein each R⁴ is H or deuterium.

13. The compound of any one of the preceding clauses, or a pharmaceutically acceptable salt thereof, wherein R⁵ is fluoro.

14. The compound of any one of the preceding clauses, or a pharmaceutically acceptable salt thereof, wherein R⁶ is H.

15. The compound of any one of the preceding clauses, or a pharmaceutically acceptable salt thereof, wherein each R⁷ is H.

16. The compound of clause 1, selected from the group consisting of

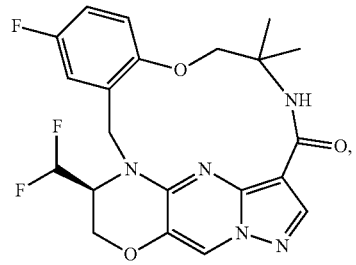

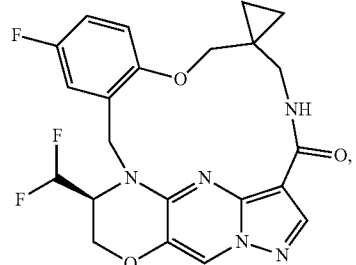

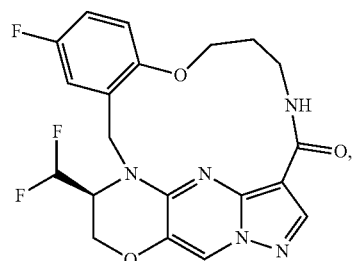

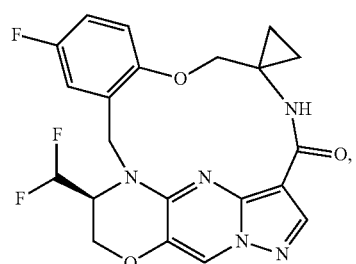

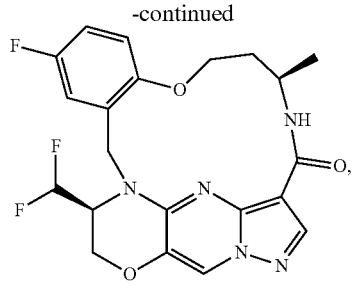

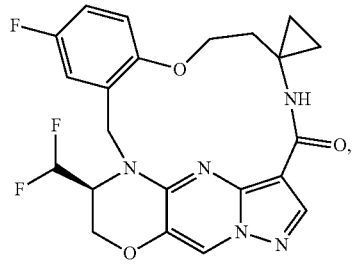

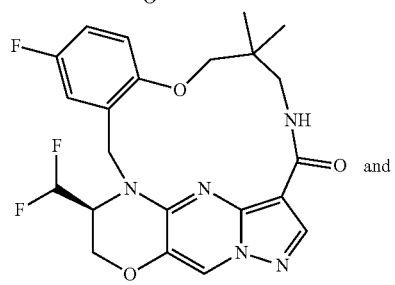

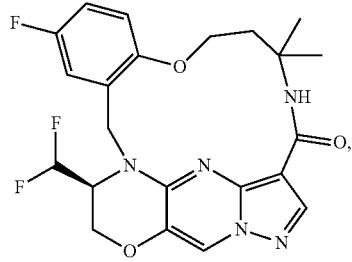

or a pharmaceutically acceptable salt thereof.

17. A pharmaceutical composition comprising a compound of any one of the preceding clauses, or a pharmaceutically acceptable salt thereof, and optionally at least one diluent, carrier or excipient.

18. A method of treating cancer, pain, neurological diseases, autoimmune diseases, or inflammation comprising administering to a subject in need of such treatment an effective amount of at least one compound of any one of clauses 1 to 16, or a pharmaceutically acceptable salt thereof.

19. The method of clause 18, wherein the disease is cancer.

20. The method of clause 18 or 19, wherein the subject is a human.

21. The method of any one of clauses 18 to 20, wherein the disease is a cancer mediated by ALK.

22. The method of any one of clauses 18 to 21, wherein the disease is a cancer mediated by a genetically altered ALK.

23. The method of any one of clauses 18 to 22, wherein the disease is a cancer mediated by a fusion protein comprising a fragment of a protein encoded by an ALK gene and a fragment of a protein encoded by a gene selected from the group consisting of NPM, EML4, TPR, TFG, ATIC, CLTC1, TPM4, MSN ALO17 and MYH9.

24. The method of clause 23, wherein the fusion protein comprises a fragment of a protein encoded by an ALK gene and a fragment of a protein encoded by an EML4 gene.

25. The method of clause 23, wherein the genetically altered ALK is an EML4-ALK fusion protein.

26. The method of clause 25, wherein the EML4-ALK fusion protein is a wild-type protein.

27. The method of clause 25, wherein the EML4-ALK fusion protein comprises at least one resistance mutation.

28. The method of clause 25, wherein the EML4-ALK fusion protein comprises at least one mutation selected from the group consisting of to L1196M, G1202R, C1156Y, D1203N, G1202 deletion, E1210K, S1206C, F1174C, F1174L, F1174S, F1174V, F1245C, G1269A, G1269S, I1171N, L1152P, L1152R, L1198F, R1275Q, S1206R, T1151-L1152insT, T1151M, V1180L, and combinations thereof.

29. The method of clause 25, wherein the EML4-ALK fusion protein comprises a mutation combination selected from the group consisting of E1210K/D1203N, E1210K/S1206C, L1198F/C1156Y, L1198F/G1202R, L1198F/L1196M, L1196M/G1202R, L1198F/C1156Y, G1202R/G1269A, and G1202R/G1269A/L1204V.

30. The method of any one of clauses 18 to 29, wherein the disease is a cancer selected from the group consisting of ALCL, NSCLC, neuroblastoma, inflammatory myofibroblastic tumor, adult renal cell carcinoma, pediatric renal cell carcinoma, breast cancer, ER$^+$ breast cancer, colonic adenocarcinoma, glioblastoma, glioblastoma multiforme, anaplastic thyroid cancer, cholangiocarcinoma, ovarian cancer, gastric adenocarcinoma, colorectal cancer, inflammatory myofibroblastic tumor, angiosarcoma, epithelioid hemangioendothelioma, intrahepatic cholangiocarcinoma, thyroid papillary cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, skin cutaneous melanoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, and serous and clear cell endometrial cancer.

31. Use of a compound of any one of clauses 1 to 16, or a pharmaceutically acceptable salt thereof, in the preparation of a medicament for the treatment of cancer.

32. Use of a compound of any one of clauses 1 to 16, or a pharmaceutically acceptable salt thereof, for treating cancer.

33. The use of clause 31 or 32, wherein the disease is a cancer mediated by ALK.

34. The use of any one of clauses 31 to 33, wherein the disease is a cancer mediated by a genetically altered ALK.

35. The use of any one of clauses 31 to 35, wherein the disease is a cancer mediated by a fusion protein comprising a fragment of a protein encoded by an ALK gene and a fragment of a protein encoded by a gene selected from the group consisting of NPM, EML4, TPR, TFG, ATIC, CLTC1, TPM4, MSN ALO17 and MYH9.

36. The use of clause 35, wherein the fusion protein comprises a fragment of a protein encoded by an ALK gene and a fragment of a protein encoded by an EML4 gene.

37. The use of clause 35, wherein the genetically altered ALK is an EML4-ALK fusion protein.

38. The use of clause 37, wherein the EML4-ALK fusion protein is a wild-type protein.

39. The use of clause 37, wherein the EML4-ALK fusion protein comprises at least one resistance mutation.

40. The use of clause 37, wherein the EML4-ALK fusion protein comprises at least one mutation selected from the group consisting of to L1196M, G1202R, C1156Y, D1203N, G1202 deletion, E1210K, S1206C, F1174C, F1174L, F1174S, F1174V, F1245C, G1269A, G1269S, I1171N, L1152P, L1152R, L1198F, R1275Q, S1206R, T1151-L1152insT, T1151M, V1180L, and combinations thereof.

41. The use of clause 37, wherein the EML4-ALK fusion protein comprises a mutation combination selected from the group consisting of E1210K/D1203N, E1210K/S1206C, L1198F/C1156Y, L1198F/G1202R, L1198F/L1196M, L1196M/G1202R, L1198F/C1156Y, G1202R/G1269A, and G1202R/G1269A/L1204V.

42. The use of any one of clauses 31 to 41, wherein the cancer selected from the group consisting of ALCL, NSCLC, neuroblastoma, inflammatory myofibroblastic tumor, adult renal cell carcinoma, pediatric renal cell carcinoma, breast cancer, ER$^+$ breast cancer, colonic adenocarcinoma, glioblastoma, glioblastoma multiforme, anaplastic thyroid cancer, cholangiocarcinoma, ovarian cancer, gastric adenocarcinoma, colorectal cancer, inflammatory myofibroblastic tumor, angiosarcoma, epithelioid hemangioendothelioma, intrahepatic cholangiocarcinoma, thyroid papillary cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, skin cutaneous melanoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, and serous and clear cell endometrial cancer.

43. A method of inhibiting ALK receptor tyrosine kinase, comprising contacting a cell comprising one or more of such kinases with an effective amount of a compound of any one of clauses 1 to 16, or a pharmaceutically acceptable salt thereof, and/or with at least one pharmaceutical composition comprising a compound of any one of clauses 1 to 16, wherein the contacting is in vitro, ex vivo, or in vivo.

44. A compound of any one of clauses 1 to 16, for use in treating cancer in a subject.

45. The compound of clause 44, wherein the disease is a cancer mediated by ALK.

46. The compound of clause 44 or 45, wherein the disease is a cancer mediated by a genetically altered ALK.

47. The compound of any one of clauses 44 to 46, wherein the disease is a cancer mediated by a fusion protein comprising a fragment of a protein encoded by an ALK gene and a fragment of a protein encoded by a gene selected from the group consisting of NPM, EML4, TPR, TFG, ATIC, CLTC1, TPM4, MSN ALO17 and MYH9.

48. The compound of clause 47, wherein the fusion protein comprises a fragment of a protein encoded by an ALK gene and a fragment of a protein encoded by an EML4 gene.

49. The compound of clause 47, wherein the genetically altered ALK is an EML4-ALK fusion protein.

50. The compound of clause 49, wherein the EML4-ALK fusion protein is a wild-type protein.

51. The compound of clause 49, wherein the EML4-ALK fusion protein comprises at least one resistance mutation.

52. The compound of clause 49, wherein the EML4-ALK fusion protein comprises at least one mutation selected from the group consisting of to L1196M, G1202R, C1156Y, D1203N, G1202 deletion, E1210K, S1206C, F1174C, F1174L, F1174S, F1174V, F1245C, G1269A, G1269S, I1171N, L1152P, L1152R, L1198F, R1275Q, S1206R, T1151-L1152insT, T1151M, V1180L, and combinations thereof.

53. The compound of clause 49, wherein the EML4-ALK fusion protein comprises a mutation combination selected from the group consisting of E1210K/D1203N, E1210K/S1206C, L1198F/C1156Y, L1198F/G1202R, L1198F/L1196M, L1196M/G1202R, L1198F/C1156Y, G1202R/G1269A, and G1202R/G1269A/L1204V.

54. The compound of any one of clauses 44 to 53, wherein the cancer selected from the group consisting of ALCL, NSCLC, neuroblastoma, inflammatory myofibroblastic tumor, adult renal cell carcinoma, pediatric renal cell carcinoma, breast cancer, ER$^+$ breast cancer, colonic adenocarcinoma, glioblastoma, glioblastoma multiforme, anaplastic thyroid cancer, cholangiocarcinoma, ovarian cancer, gastric adenocarcinoma, colorectal cancer, inflammatory myofibroblastic tumor, angiosarcoma, epithelioid hemangioendothelioma, intrahepatic cholangiocarcinoma, thyroid papillary cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, skin cutaneous melanoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, and serous and clear cell endometrial cancer.

DETAILED DESCRIPTION

Figure 1A:
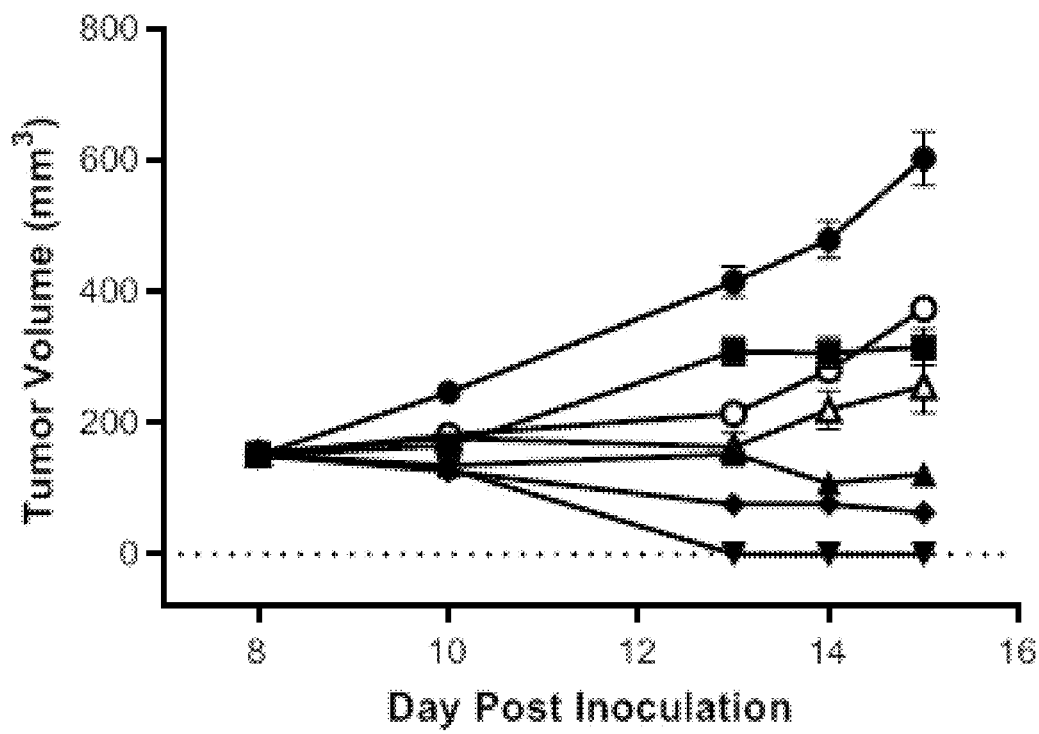
FIG. 1A shows tumor volumes of xenograft tumor models in mice bearing Ba/F3 cell derived xenograft tumors harboring an EML4-ALK fusion with a G1202R mutation. (●) vehicle; (■) Compound 1 (2 mg/kg BID); (▲) Compound 1 (5 mg/kg BID); (▼) Compound 1 (10 mg/kg BID); (○) Compound 2 (3 mg/kg BID); (Δ) Compound 2 (10 mg/kg BID); (♦) Lorlatinib (5 mg/kg).

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e., C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e., CC). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkynyl may be unsubstituted, or substituted as described for alkyl or as described in the various embodiments provided herein. Illustrative alkynyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthylenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, or a carbocyclic ring that is fused to another group such as a heterocyclic, such as ring 5- or 6-membered cycloalkyl fused to a 5- to 7-membered heterocyclic ring, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

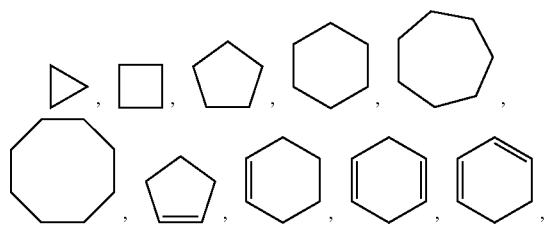

-continued

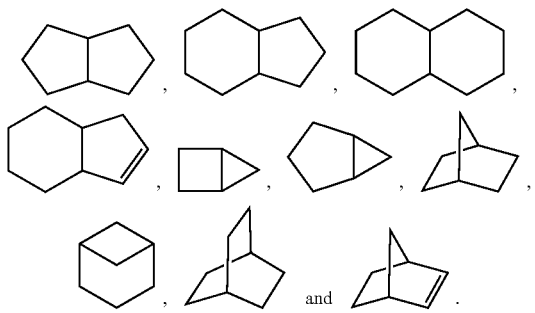

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. A heterocycloalkyl group may be fused to another group such as another heterocycloalkyl, or a heteroaryl group. Heterocycloalkyl may also have one of more double bonds, including double bonds to nitrogen (e.g., C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, 3-, 4-, 5- or 6-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

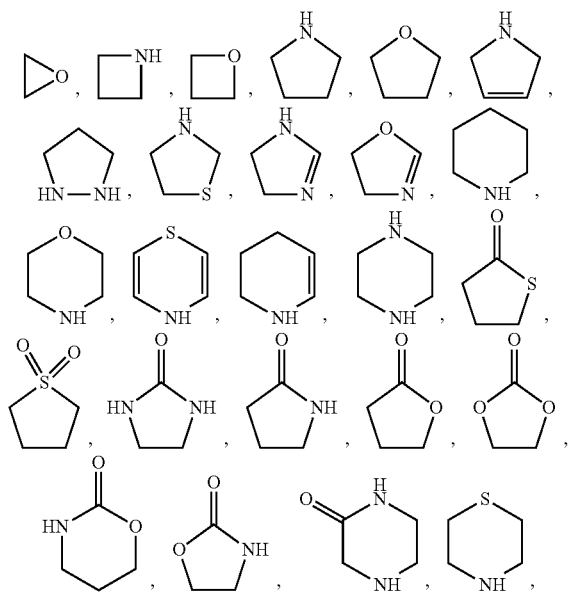

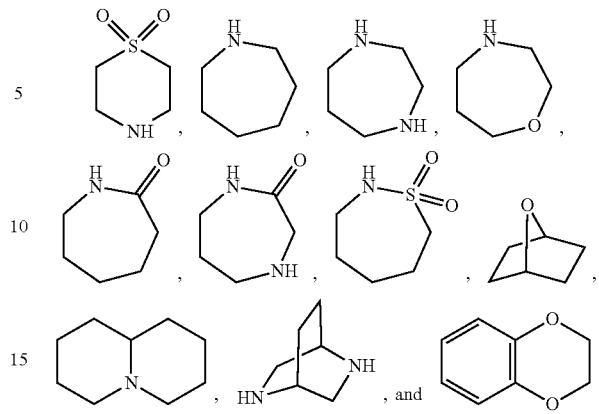

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

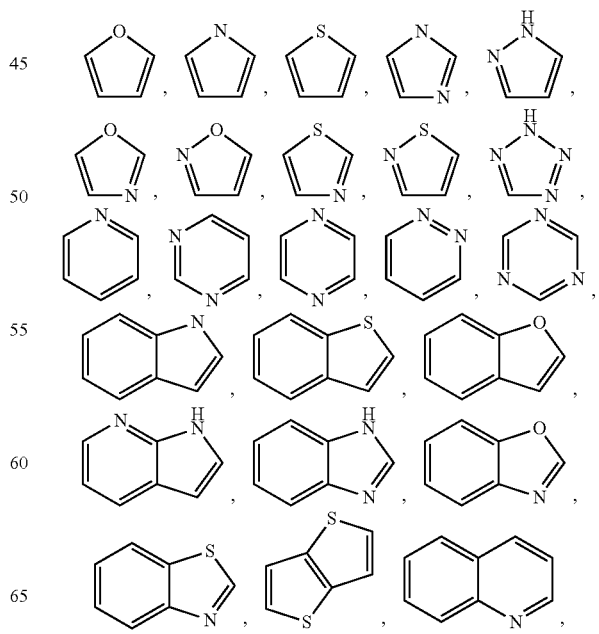

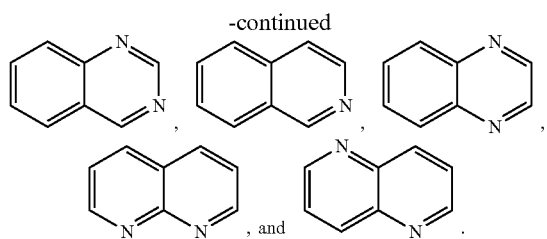

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the phrase "taken together with the carbon atom to which they are attached" or "taken together with the carbon atom to which they are attached" means that two substituents (e.g., $R^1$ and $R^2$) attached to the same carbon atom form the groups that are defined by the claim, such as $C_3$-$C_6$ cycloalkyl. In particular, the phrase "taken together with the carbon atom to which they are attached" means that when, for example, $R^1$ and $R^2$, and the carbon atom to which they are attached form a $C_3$-$C_6$ cycloalkyl, then the formed ring will be attached at the same carbon atom. For example, the phrase "$R^1$ and $R^2$ taken together with the carbon atom to which they are attached form a $C_3$-$C_6$ cycloalkyl" used in connection with the embodiments described herein includes the compounds represented as follows:

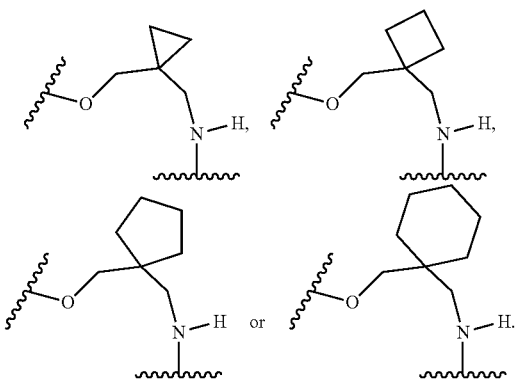

where the above spirocyclic rings can be optionally substituted as defined in the given embodiment.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula I-IIIA that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds of Formula I-IIIA, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I-IIIA). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure also relates to pharmaceutically active metabolites of compounds of Formula I-IIIA, and uses of such metabolites in the methods of the disclosure. A "pharmaceutically active metabolite" means a pharmacologically active product of metabolism in the body of a compound of Formula I-IIIA, or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, Drug Dev. Res. 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol "〜〜" include both stereoisomers for the carbon atom to which the symbol "〜〜" is attached, specifically both the bonds "━◀" and "⋯⋯" are encompassed by the meaning of "〜〜". For example, in some exemplary embodiments, certain compounds provided herein can be described by the formula

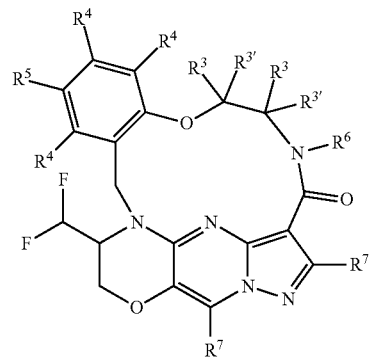

which formula will be understood to encompass compounds having both stereochemical configurations at the relevant carbon atom, specifically in this example

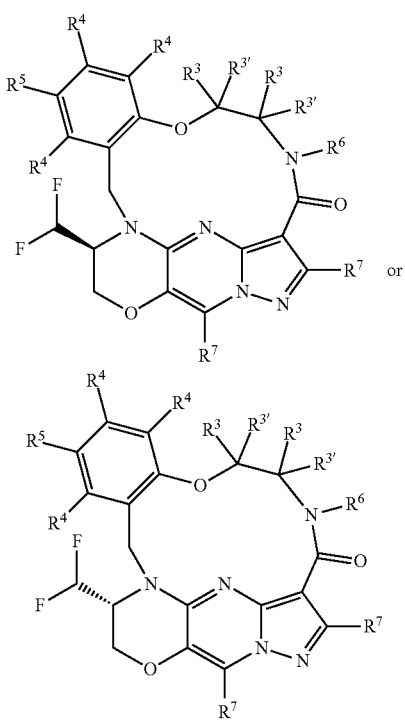

and other stereochemical combinations depending on the identity of each $R^3$ and $R^{3'}$.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of subjects. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

As used herein, "ALK" refers to anaplastic lymphoma kinase, which along with leukocyte tyrosine kinase (LTK), belongs to the insulin receptor (IR) superfamily of receptor tyrosine kinases. It will be appreciated that ALK refers to the ALK gene, the corresponding mRNA transcribed from the ALK gene, the protein product of translation of the corresponding mRNA, as well as each of the aforementioned involving the rearrangement or fusion of a portion of ALK with another gene or gene product, including but not limited to NPM, EML4, TPR, TFG, ATIC, CLTC1, TPM4, MSN, ALO17, MYH9, and the like. Furthermore, it will be appreciated that "ALK" refers to mutations in the ALK gene, or the ALK protein, that can be the result of acquired resistance mechanisms to treatment with ALK inhibitors, as described above. It will be appreciated that the ALK mutation is not necessarily dependent on the identity of the rearrangement or fusion partner, e.g. EML4, NPM, and the like, and that the mutation can be, for example a missense mutation, an insertion, or a deletion that occurs in the ALK portion of the ALK rearrangement or fusion protein. Examples of mutation sites include, but are not limited to L1196, L1198, G1202, D1203, 51206, T1151, L1152, E1210, F1174, C1156, I1171, V1180, F1245, G1269, R1275, and the like, and combinations thereof. Examples of ALK mutations include but are not limited to L1196M, G1202R, C1156Y, D1203N, G1202 deletion, E1210K, 51206C, F1174C, F1174L, F1174S, F1174V, F1245C, G1269A, G1269S, I1171N, L1152P, L1152R, L1198F, R1275Q, 51206R, T1151-L1152insT, T1151M, V1180L, and the like, and combinations thereof. Examples of multiple ALK mutations include but are not limited to E1210K/D1203N, E1210K1S1206C, L1198F/C1156Y, L1198F/G1202R, L1198F/L1196M, L1196M/G1202R, L1198F/C1156Y, G1202R/G1269A, G1202R/G1269A/L1204V and the like.

As used herein, the term "cancer" includes, but is not limited to, ALCL, NSCLC, neuroblastoma, inflammatory myofibroblastic tumor, adult renal cell carcinoma, pediatric renal cell carcinoma, breast cancer, $ER^+$ breast cancer, colonic adenocarcinoma, glioblastoma, glioblastoma multiforme, anaplastic thyroid cancer, cholangiocarcinoma, ovarian cancer, gastric adenocarcinoma, colorectal cancer, inflammatory myofibroblastic tumor, angiosarcoma, epithelioid hemangioendothelioma, intrahepatic cholangiocarcinoma, thyroid papillary cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, skin cutaneous melanoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, and serous and clear cell endometrial cancer.

Representative Embodiments

In some embodiments, each $R^1$ and $R^2$ is independently H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, mono- or bicyclic heteroaryl, —$OR^a$, —$OC(O)R^a$, —$OC(O)R^a$, —$OC(O)NR^aR^b$, —$OS(O)R^a$, —$OS(O)_2R^a$, —$SR^a$, —$S(O)R^a$, —$S(O)_2R^a$, —$S(O)NR^aR^b$, —$S(O)_2NR^aR^b$, —$OS(O)NR^aR^b$, —$OS(O)_2NR^aR^b$, —$NR^aR^b$, —$NR^aC(O)R^b$, —$NR^aC(O)OR^b$, —$NR^aC(O)NR^aR^b$, —$NR^aS(O)R^b$, —$NR^aS(O)_2R^b$, —$NR^aS(O)NR^aR^b$, —$NR^aS(O)_2NR^aR^b$, —$C(O)R^a$, —$C(O)OR^a$, —$C(O)NR^aR^b$, —$PR^aR^b$, —$P(O)R^aR^b$, —$P(O)_2R^aR^b$, —$P(O)NR^aR^b$, —$P(O)_2NR^aR^b$, —$P(O)OR^a$, —$P(O)_2OR^a$, —CN, or —$NO_2$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, and mono- or bicyclic heteroaryl is independently optionally substituted by deuterium, halogen, $C_1$-$C_6$ alkyl, $C_1$-$C_6$ haloalkyl, —$OR^e$, —$OC(O)R^e$, —$OC(O)NR^eR^f$, —$OC(\!\!=\!\!N)NR^eR^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$. In some embodiments, R$^1$ and R$^2$ taken together with the carbon atom to which they are attached combine to form a C$_3$-C$_6$ cycloalkyl. In some embodiments, each R$^1$ and R$^2$, when present, is independently H, deuterium, C$_1$-C$_6$ alkyl.

In some embodiments, each R$^3$ and R$^{3'}$ is independently H, deuterium, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, mono- or bicyclic heteroaryl, —OR$^a$, —OC(O)R$^a$, —OC(O)R$^a$, —OC(O)NR$^a$R$^b$, —OS(O)R$^a$, —OS(O)$_2$R$^a$, —SR$^a$, —S(O)R$^a$, —S(O)$_2$R$^a$, —S(O)NR$^a$R$^b$, —S(O)$_2$NR$^a$R$^b$, —OS(O)NR$^a$R$^b$, —OS(O)$_2$NR$^a$R$^b$, —NR$^a$R$^b$, —NR$^a$C(O)R$^b$, —NR$^a$C(O)OR$^b$, —NR$^a$C(O)NR$^a$R$^b$, —NR$^a$S(O)R$^b$, —NR$^a$S(O)$_2$R$^b$, —NR$^a$S(O)NR$^a$R$^b$, —NR$^a$S(O)$_2$NR$^a$R$^b$, —C(O)R$^a$, —C(O)OR$^a$, —C(O)NR$^a$R$^b$, —PR$^a$R$^b$, —P(O)R$^a$R$^b$, —P(O)$_2$R$^a$R$^b$, —P(O)NR$^a$R$^b$, —P(O)$_2$NR$^a$R$^b$, —P(O)OR$^a$, —P(O)$_2$OR$^a$, —CN, or —NO$_2$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, mono- or bicyclic heteroaryl, is independently optionally substituted by deuterium, halogen, C$_1$-C$_6$ alkyl, C$_1$-C$_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$. In some embodiments, R$^3$ and R$^{3'}$ taken together with the carbon atom to which they are attached combine to form a C$_3$-C$_6$ cycloalkyl, wherein each hydrogen atom in C$_3$-C$_6$ cycloalkyl is independently optionally substituted by deuterium, halogen, C$_1$-C$_6$ alkyl, C$_1$-C$_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$. In some embodiments, each R$^3$ and R$^{3'}$ is independently H, deuterium, C$_1$-C$_6$ alkyl. In some embodiments, R$^3$ and R$^{3'}$ taken together with the carbon atom to which they are attached combine to form a C$_3$-C$_6$ cycloalkyl. In some embodiments, each R$^{3'}$ is H or deuterium. In some embodiments, both R$^{3'}$ taken together combine to form a divalent group —(CR$^1$R$^2$)$_m$—, where m is 1 or 2.

In some embodiments, each R$^4$ and R$^5$ is independently hydrogen, deuterium, halogen, —OW, —OC(O)R$^c$, —OC(O)NR$^c$R$^d$, —OC(=N)NR$^c$R$^d$, —OS(O)R$^c$, —OS(O)$_2$R$^c$, —OS(O)NR$^c$R$^d$, —OS(O)$_2$NR$^c$R$^d$, —SR$^c$, —S(O)R$^c$, —S(O)$_2$R$^c$, —S(O)NR$^c$R$^d$, —S(O)$_2$NR$^c$R$^d$, —NR$^c$R$^d$, —NR$^c$C(O)R$^d$, —NR$^c$C(O)OR$^d$, —NR$^c$C(O)NR$^c$R$^d$, —NR$^c$C(=N)NR$^c$R$^d$, —NR$^c$S(O)R$^d$, —NR$^c$S(O)$_2$R$^d$, —NR$^c$S(O)NR$^c$R$^d$, —NR$^c$S(O)$_2$NR$^c$R$^d$, —C(O)R$^c$, —C(O)OR$^c$, —C(O)NR$^c$R$^d$, —C(=N)NR$^c$R$^d$, —PR$^c$R$^d$, —P(O)R$^c$R$^d$, —P(O)$_2$R$^c$R$^d$, —P(O)NR$^c$R$^d$, —P(O)$_2$NR$^c$R$^d$, —P(O)OR, —P(O)$_2$OR$^c$, —CN, —NO$_2$, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, mono- or bicyclic heteroaryl, C$_5$-C$_8$ cycloalkyl, or 5- to 8-membered heterocycloalkyl is independently optionally substituted by deuterium, halogen, C$_1$-C$_6$ alkyl, C$_1$-C$_6$ haloalkyl, —OR$^e$, —OC(O)R$^e$, —OC(O)NR$^e$R$^f$, —OC(=N)NR$^e$R$^f$, —OS(O)R$^e$, —OS(O)$_2$R$^e$, —OS(O)NR$^e$R$^f$, —OS(O)$_2$NR$^e$R$^f$, —SR$^e$, —S(O)R$^e$, —S(O)$_2$R$^e$, —S(O)NR$^e$R$^f$, —S(O)$_2$NR$^e$R$^f$, —NR$^e$R$^f$, —NR$^e$C(O)R$^f$, —NR$^e$C(O)OR$^f$, —NR$^e$C(O)NR$^e$R$^f$, —NR$^e$S(O)R$^f$, —NR$^e$S(O)$_2$R$^f$, —NR$^e$S(O)NR$^e$R$^f$, —NR$^e$S(O)$_2$NR$^e$R$^f$, —C(O)R$^e$, —C(O)OR$^e$, —C(O)NR$^e$R$^f$, —PR$^e$R$^f$, —P(O)R$^e$R$^f$, —P(O)$_2$R$^e$R$^f$, —P(O)NR$^e$R$^f$, —P(O)$_2$NR$^e$R$^f$, —P(O)OR$^e$, —P(O)$_2$OR$^e$, —CN, or —NO$_2$. In some embodiments, each R$^4$ is H or deuterium. In some embodiments, R$^5$ is fluoro.

In some embodiments, R$^6$ is H, deuterium, or C$_1$-C$_6$ alkyl, wherein each hydrogen atom in C$_1$-C$_6$ alkyl is independently optionally substituted by deuterium, halogen, —OR$^e$, —SR$^e$, or —NR$^e$R$^f$. In some embodiments, R$^6$ is H.

In some embodiments, each R$^7$ is independently hydrogen or deuterium. In some embodiments, R$^7$ is H.

In some embodiments, each R$^a$, R$^b$, R$^c$, R$^d$, R$^e$, and R$^f$ is independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3-to 7-membered heterocycloalkyl, C$_6$-C$_{10}$ aryl, and 5- to 7-membered heteroaryl.

In some embodiments, n is 0, 1, 2, or 3. In some embodiments, n is 0 or 1. In some embodiments, n is 0. In some embodiments, n is 1.

The following represent illustrative embodiments of compounds of the Formula I-IIIA:

| Cpd | Structure | Name |
|---|---|---|
| 1 | 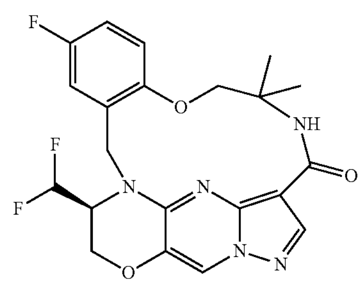 [SMILES: CC1(C)COc2ccc(F)cc2CN2c3nc4c(cnn4cc3OC[C@H]2C(F)F)C(=O)N1] | (4S)-4-(Difluoromethyl)-8-fluoro-13,13-dimethyl-3,4,13,14-tetrahydro-6H-18,1-(metheno)[1,4]oxazino[3,4-i]pyrazolo[4,3-f][1,4,8,10]benzoxatriazacyclotridecin-15(12H)-one a.k.a. (S,14aE,15aE)-13-(difluoromethyl)-35-fluoro-6,6-dimethyl-13,14-dihydro-12H-4-oxa-7-aza-1(4,6)-pyrazolo[1',5':1,2]pyrimido[5,4-b][1,4]oxazina-3(1,2)-benzenacyclooctaphan-8-one |

-continued

| Cpd | Structure | Name |
|---|---|---|
| 2 | 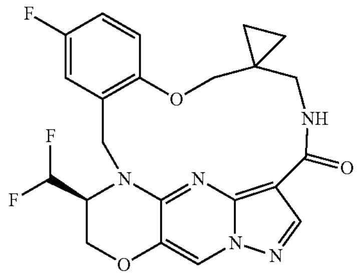 [SMILES: O=C1NCC2(CC2)COc2ccc(F)cc2CN2c3nc4c1cnn4cc3OC[C@H]2C(F)F] | (16'S)-16'-(Difluoromethyl)-12'-fluoro-4'H,5'H,6'H,8'H,14'H,16'H,17'H-spiro[cyclopropane-1,7'-[1,19](metheno)[1,4]oxazino[3,4-j]pyrazolo[4,3-g][1,5,9,11]benzoxatriazacyclotetradecin]-4'-one a.k.a (S,4a'E,5a'E)-3'-(difluoromethyl)-5'-fluorospiro[cyclopropane-1,6'-4-oxa-8-aza-1(4,6)-pyrazolo[1',5':1,2]pyrimido[5,4-b][1,4]oxazina-3(1,2)-benzenacyclononaphan]-9'-one |
| 3 | 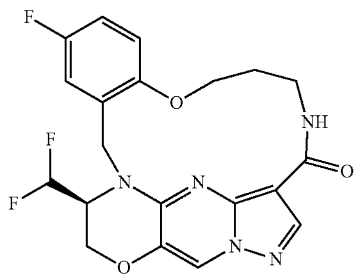 [SMILES: O=C1NCCCOc2ccc(F)cc2CN2c3nc4c1cnn4cc3OC[C@H]2C(F)F] | (16S)-16-(Difluoromethyl)-12-fluoro-5,6,7,8,16,17-hexahydro-4H,14H-1,19-(metheno)[1,4]oxazino[3,4-j]pyrazolo[4,3-j][1,5,9,11]benzoxatriazacyclotetradecin-4-one a.k.a (S,14aE,15aE)-13-(difluoromethyl)-35-fluoro-13,14-dihydro-12H-4-oxa-8-aza-1(4,6)-pyrazolo[1',5':1,2]pyrimido[5,4-b][1,4]oxazina-3(1,2)-benzenacyclononaphan-9-one |
| 4 | 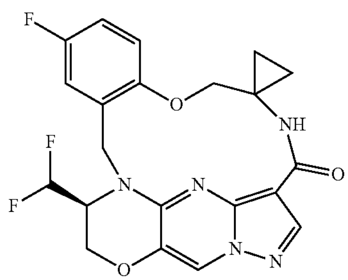 [SMILES: O=C1NC2(CC2)COc2ccc(F)cc2CN2c3nc4c1cnn4cc3OC[C@H]2C(F)F] | (4'S)-4'-(Difluoromethyl)-8'-fluoro-3'H,4'H,6'H,12'H,14'H,15'H-spiro[cyclopropane-1,13'-[18,1](metheno)[1,4]oxazino[3,4-i]pyrazolo[4,3-f][1,4,8,10]benzoxatriazacyclotridecin]-15'-one a.k.a (S,4a'E,5a'E)-3'-(difluoromethyl)-5'-fluorospiro[cyclopropane-1,6'-4-oxa-7-aza-1(4,6)-pyrazolo[1',5':1,2]pyrimido[5,4-b][1,4]oxazina-3(1,2)-benzenacyclooctaphan]-8'-one |
| 5 | 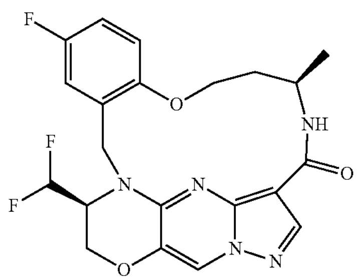 [SMILES: C[C@@H]1CCOc2ccc(F)cc2CN2c3nc4c(cnn4cc3OC[C@H]2C(F)F)C(=O)N1] | (6R,16S)-16-(Difluoromethyl)-12-fluoro-6-methyl-5,6,7,8,16,17-hexahydro-4H,14H-1,19-(metheno)[1,4]oxazino[3,4-j]pyrazolo[4,3-g][1,5,9,11]benzoxatriazacyclotetradecin-4-one a.k.a (13S,14aE,15aE,7R)-13-(difluoromethyl)-35-fluoro-7-methyl-13,14-dihydro-12H-4-oxa-8-aza-1(4,6)-pyrazolo[1',5':1,2]pyrimido[5,4-b][1,4]oxazina-3(1,2)-benzenacyclononaphan-9-one |
| 6 | 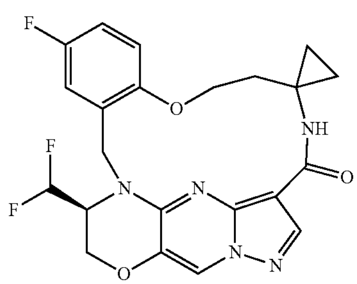 [SMILES: O=C1NC2(CCOc3ccc(F)cc3CN3c4nc5c1cnn5cc4OC[C@H]3C(F)F)CC2] | (16'S)-16'-(Difluoromethyl)-12'-fluoro-4'H,5'H,7'H,8'H,14'H,16'H,17'H-spiro[cyclopropane-1,6'-[1,19](metheno)[1,4]oxazino[3,4-j]pyrazolo[4,3-g][1,5,9,11]benzoxatriazacyclotetradecin]-4'-one a.k.a (S,4a'E,5a'E)-3'-(difluoromethyl)-5'-fluorospiro[cyclopropane-1,7'-4-oxa-8-aza-1(4,6)-pyrazolo[1',5':1,2]pyrimido[5,4-b][1,4]oxazina-3(1,2)-benzenacyclononaphan]-9'-one |

| Cpd | Structure | Name |
|---|---|---|
| 7 | 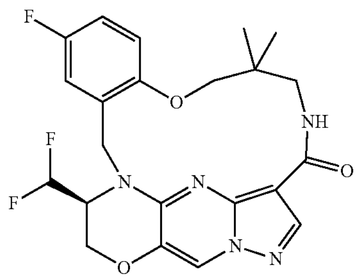 [SMILES: CC1(C)CNC(=O)c2cnn3cc4c(nc23)N(Cc2cc(F)ccc2OC1)[C@H](C(F)F)CO4] | (16S)-16-(Difluoromethyl)-12-fluoro-7,7-dimethyl-5,6,7,8,16,17-hexahydro-4H,14H-1,19-(metheno)[1,4]oxazino[3,4-j]pyrazolo[4,3-g][1,5,9,11]benzoxatriazacyclotetradecin-4-one a.k.a. (S,14aE,15aE)-13-(difluoromethyl)-35-fluoro-6,6-dimethyl-13,14-dihydro-12H-4-oxa-8-aza-1(4,6)-pyrazolo[1',5':1,2]pyrimido[5,4-b][1,4]oxazina-3(1,2)-benzenacyclononaphan-9-one |
| 8 | 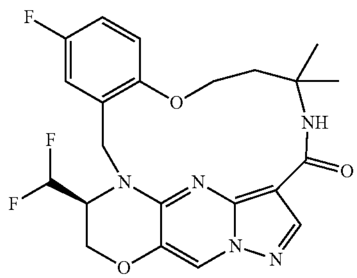 [SMILES: CC1(C)CCOc2ccc(F)cc2CN2c3nc4c(cnn4cc3OC[C@H]2C(F)F)C(=O)N1] | (16S)-16-(Difluoromethyl)-12-fluoro-6,6-dimethyl-5,6,7,8,16,17-hexahydro-4H,14H-1,19-(metheno)[1,4]oxazino[3,4-j]pyrazolo[4,3-g][1,5,9,11]benzoxatriazacyclotetradecin-4-one a.k.a. (S,14aE,15aE)-13-(difluoromethyl)-35-fluoro-7,7-dimethyl-13,14-dihydro-12H-4-oxa-8-aza-1(4,6)-pyrazolo[1',5':1,2]pyrimido[5,4-b][1,4]oxazina-3(1,2)-benzenacyclononaphan-9-one |

Those skilled in the art will recognize that the species listed or illustrated herein are not exhaustive, and that additional species within the scope of these defined terms may also be selected.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human, or, in the case of veterinary applications, can be a laboratory, agricultural, or domestic animal. In some embodiments, the subject can be a human. In some embodiments, the subject can be a domestic animal for veterinary uses, such as a dog or cat. In some embodiments, the subject can be an agricultural animal, sush as a cow, pig, horse, and the like. In some embodiments, the subject can be a laboratory animal such as a rodent (e.g. mouse, rat, etc), primate (e.g. rhesus monkey, and the like), a canine, and the like.

Exemplary diseases include cancer, pain, neurological diseases, autoimmune diseases, and inflammation. Cancer includes, for example, lung cancer, colon cancer, breast cancer, prostate cancer, hepatocellular carcinoma, renal cell carcinoma, gastric and esophago-gastric cancers, glioblastoma, head and neck cancers, inflammatory myofibroblastic tumors, and anaplastic large cell lymphoma. Pain includes, for example, pain from any source or etiology, including cancer pain, pain from chemotherapeutic treatment, nerve pain, pain from injury, or other sources. Autoimmune diseases include, for example, rheumatoid arthritis, Sjogren syndrome, Type I diabetes, and lupus. Exemplary neurological diseases include Alzheimer's Disease, Parkinson's Disease, Amyotrophic lateral sclerosis, and Huntington's disease. Exemplary inflammatory diseases include atherosclerosis, allergy, and inflammation from infection or injury.

In one aspect, the compounds and pharmaceutical compositions of the invention specifically target tyrosine receptor kinases, in particular ALK, more particularly ALK having one or more mutations as described herein. Thus, these compounds and pharmaceutical compositions can be used to prevent, reverse, slow, or inhibit the activity of ALK. In preferred embodiments, methods of treatment target cancer. In other embodiments, methods are for treating lung cancer, particularly non-small cell lung cancer.

In the inhibitory methods of the invention, an "effective amount" means an amount sufficient to inhibit the target protein. Measuring such target modulation may be performed by routine analytical methods such as those described below. Such modulation is useful in a variety of settings, including in vitro assays. In such methods, the cell is preferably a cancer cell with abnormal signaling due to upregulation of ALK, in particular particularly ALK having one or more mutations as described herein.

In some embodiments, the uses and methods described herein for any compound for the Formula I-IIIa can be for treating cancer mediated by ALK or mediated by a rearrangement or fusion of ALK with another gene or gene product, including but not limited to NPM, EML4, TPR, TFG, ATIC, CLTC1, TPM4, MSN, ALO17, MYH9, and the like. In some embodiments, the uses and methods described herein for any compound for the Formula I-IIIa can be for treating cancer mediated by ALK or mediated by a rearrangement or fusion of ALK with another gene or gene product, including but not limited to NPM, EML4, TPR, TFG, ATIC, CLTC1, TPM4, MSN, ALO17, MYH9, and the like, and having at least one mutation, such as a missense mutation, an insertion, or a deletion that occurs in the ALK portion of the ALK rearrangement or fusion protein, wherein the mutation site includes, but is not limited to L1196, L1198, G1202, D1203, 51206, T1151, L1152, E1210, F1174, C1156, I1171, V1180, F1245, G1269, R1275, and the like, and combinations thereof.

In some embodiments, the uses and methods described herein for any compound for the Formula I-IIIa can be for treating cancer mediated by ALK or mediated by a rearrangement or fusion of ALK with another gene or gene product, including but not limited to NPM, EML4, TPR, TFG, ATIC, CLTC1, TPM4, MSN, ALO17, MYH9, and the like, and having at least one mutation, such as a missense mutation, an insertion, or a deletion that occurs in the ALK portion of the ALK rearrangement or fusion protein, wherein the ALK mutation is L1196M, G1202R, C1156Y, D1203N, G1202 deletion, E1210K, S1206C, F1174C, F1174L, F1174S, F1174V, F1245C, G1269A, G1269S, I1171N, L1152P, L1152R, L1198F, R1275Q, S1206R, T1151-L1152insT, T1151M, V1180L, or the like, and combinations thereof. In some embodiments, the uses and methods described herein for any compound for the Formula I-IIIa can be for treating cancer mediated by ALK or mediated by a rearrangement or fusion of ALK with another gene or gene product, including but not limited to NPM, EML4, TPR, TFG, ATIC, CLTC1, TPM4, MSN, ALO17, MYH9, and the like, and having at least one mutation, such as a missense mutation, an insertion, or a deletion that occurs in the ALK portion of the ALK rearrangement or fusion protein, wherein the mutation is a multiple ALK mutation selected from E1210K/D1203N, E1210K/S1206C, L1198F/C1156Y, L1198F/G1202R, L1198F/L1196M, L1196M/G1202R, L1198F/C1156Y, G1202R/G1269A, and G1202R/G1269A/L1204V.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

Once improvement of the subject's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Subjects may, however, require intermittent treatment on a long-term basis upon any recurrence of symptoms. Subjects may also require chronic treatment on a long-term basis.

Drug Combinations

The inventive compounds described herein may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Combination agents include additional active ingredients are those that are known or discovered to be effective in treating the diseases and disorders described herein, including those active against another target associated with the disease. For example, compositions and formulations of the invention, as well as methods of treatment, can further comprise other drugs or pharmaceuticals, e.g., other active agents useful for treating or palliative for the target diseases or related symptoms or conditions. For cancer indications, additional such agents include, but are not limited to, kinase inhibitors, such as EGFR inhibitors (e.g., erlotinib, gefitinib), Raf inhibitors (e.g., vemurafenib), VEGFR inhibitors (e.g., sunitinib), ALK inhibitors (e.g., crizotinib) standard chemotherapy agents such as alkylating agents, antimetabolites, anti-tumor antibiotics, topoisomerase inhibitors, platinum drugs, mitotic inhibitors, antibodies, hormone therapies, or corticosteroids. For pain indications, suitable combination agents include anti-inflammatories such as NSAIDs. The pharmaceutical compositions of the invention may additionally comprise one or more of such active agents, and methods of treatment may additionally comprise administering an effective amount of one or more of such active agents.

Chemical Synthesis

Exemplary chemical entities useful in methods of the description will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Abbreviations

The examples described herein use materials, including but not limited to, those described by the following abbreviations known to those skilled in the art:

| | |
|---|---|
| g | grams |
| eq | equivalents |
| mmol | millimoles |
| mL | milliliters |
| EtOAc or EA | ethyl acetate |
| MHz | megahertz |
| Ppm | parts per million |
| Δ | chemical shift |
| S | singlet |
| D | doublet |
| T | triplet |
| Q | quartet |
| Quin | quintet |
| Br | broad |
| M | multiplet |
| Hz | hertz |
| THF | tetrahydrofuran |
| °C. | degrees Celsius |
| $R_f$ | retardation factor |
| N | normal |
| J | coupling constant |
| DMSO-d6 | deuterated dimethyl sulfoxide |
| EtOH | ethanol |
| DIPEA | N,N-diisopropylethylamine |
| min | minutes |
| hr | hours |
| TLC | thin layer chromatography |
| M | molar |
| MS | mass spectrum |
| m/z | mass-to-charge ratio |
| DMAP | 4-(dimethylamino)pyridine |
| μM | micromolar |
| $IC_{50}$ | half maximal inhibitory concentration |
| U/mL | units of activity per milliliter |
| MOM-Cl | methoxymethyl chloride |
| DCM | dichloromethane |
| DMF | N,N-dimethylformamide |

EXAMPLES

Comparative Examples

Comparative Examples 1 and 2 were made as described in International PCT Publication No. WO 2019126122, corresponding to International PCT Application No. PCT/US2018/066159, filed Dec. 18, 2018.

| Comparative Example | Structure |
|---|---|
| Comp. Ex. 1 | 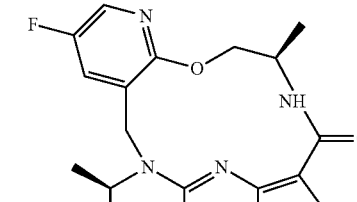 |
| Comp. Ex. 2 | 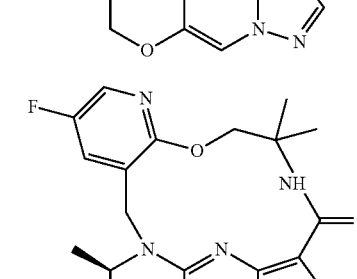 |

Example 1: General Method A

Preparation of tert-Butyl {1-[2-(chloromethyl)-4-fluorophenoxy]-2-methylpropan-2-yl}carbamate (A-1)

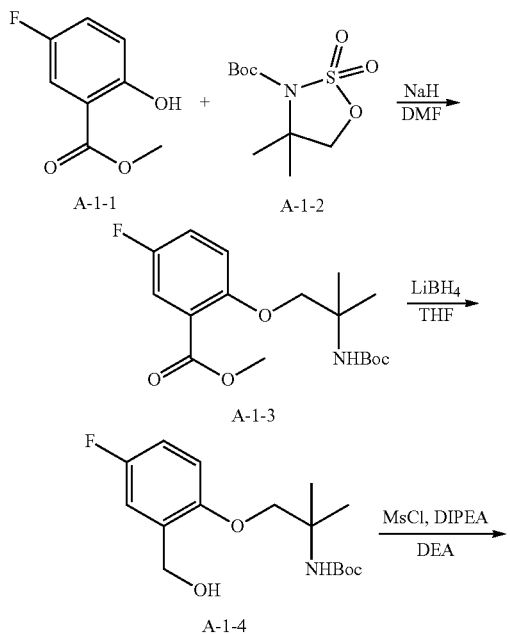

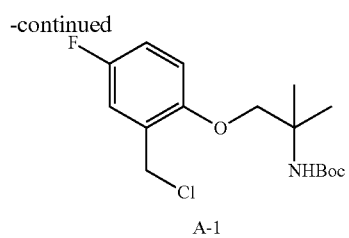

Step 1: To A-1-1 (259 mg, 1.52 mmol) in anhydrous DMF (7.35 mL) was added NaH (60% in mineral oil, 91.3 mg, 2.28 mmol) under argon at 0° C. The reaction was allowed to stir and warm over 1 hr. The reaction was cooled to 0° C. and A-1-2 was added. The reaction was stirred and the temperature was increased to 50° C. and stirred for 18 hr. The reaction was quenched with saturated $NH_4Cl$ (aq. 5 mL) at 0° C. and stirred vigorously. Water (25 mL) was added and extracted with DCM (3×25 mL). The combined organic layer was washed with brine and dried over sodium sulfate. Flash column chromatography (12 g silica, ISCO, 0-50% EA in Hexanes) provided A-1-3 (267 mg, 51% yield).

Step 2: to A-1-3 (267 mg, 0.782 mmol) in anhydrous THF (3.9 mL) was added $LiBH_4$ (34 mg, 1.56 mmol) at 0° C. The reaction was stirred for 18 hr as temperature increased to ambient. The reaction was quenched with water (5 mL) and 2 M NaOH (1 mL), then extracted with DCM (3×10 mL). The combined organic layer was washed with brine and dried over sodium sulfate. Flash column chromatography (12 g silica, ISCO, 0-50% EA in Hexanes with ELSD detection) provided A-1-4 (29.3 mg, 12% yield).

Step 3: To A-1-4 (29.3 mg, 93.5 μmol) in DCM (1 mL) was added Hunig's base (36.2 mg, 280.5 μmol, 48.8 μL). The reaction was cooled to 0° C. and mesyl chloride (13.9 mg, 121.5 μmol, 9.4 uL) was added. The reaction was stirred as temperature increase to 0-22° C. over 18 hr. The reaction was quenched with 2 M HCl(aq) (1 mL) at 0° C. Diluted with water and DCM (5 mL each), layers were partitioned and the aqueous layer was extracted DCM (2×5 mL). The combined organic layer was washed with brine and dried over sodium sulfate. Flash column chromatography (12 g silica, ISCO, 0-50% EA in Hex) to afford A-1 (25.2 mg, 75.9 μmol, 81% yield).

Example 2: General Method B

Preparation of tert-Butyl [(1-{[2-(chloromethyl)-4-fluorophenoxy]methyl}cyclopropyl) methyl]carbamate (A-2)

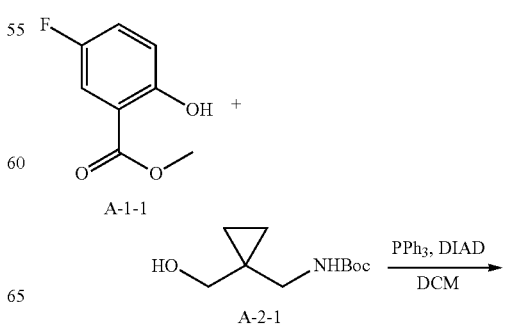

-continued

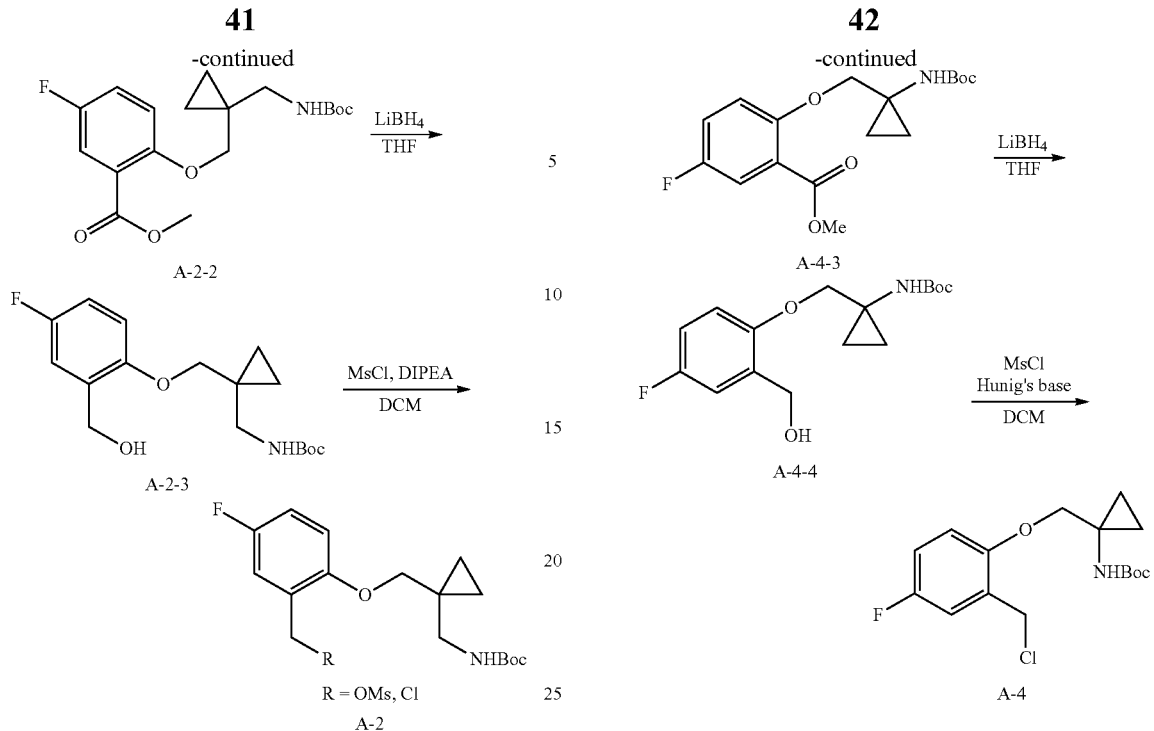

Step 1: To a solution of A-1-1 (100 mg, 587.7 µmol), A-2-1 (118.2 mg, 587.7 µmol), and PPh₃ (231.2 mg, 881.6 µmol) in anhydrous DCM (403.14 µL) at 0° C. was added DIAD (190.2 mg, 940.4 µmol, 184.6 µL) with stirring. The mixture was stirred for 18 hr as it warmed to RT. Flash column chromatography (ISCO, 12 g silica, 0-50% ethyl acetate in hexanes) provided A-2-2 (163.1 mg, 433.3 µmol, 73.7% yield)

Step 2: Compound A-2 was prepared according to General Method A starting with B-1-2 in step 2.

Compound A-3 was prepared according to General Method B

Compound A-5, A-6, A-7, and A-8 were prepared according to General Method B

Example 3: General Method C

Preparation of tert-butyl (1-((2-(chloromethyl)-4-fluorophenoxy)methyl)cyclopropyl)carbamate (A-4)

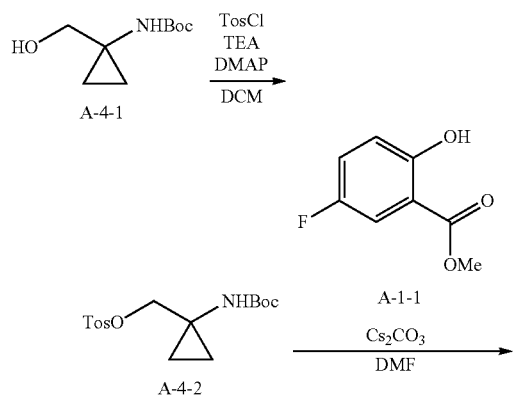

Compound A-4 was prepared according to General Method C

Step 1. To a solution of A-4-1 (500 mg, 2.67 mmol) in DCM (12.25 mL) was added triethylamine (811 mg, 8.0 mmol, 1.12 mL). The mixture was cooled to 0° C. and p-toluenesulfonyl chloride (TosCl, 611 mg, 3.2 mmol) and DMAP (6.5 mg, 53 µmol) were added. The reaction was warmed to 22° C. and stirred for 18 hr. Water (15 mL) and DCM (10 mL) were added and the organic layer separated. The aqeuous layer was extracted with DCM (2×10 mL), dried with Na₂SO₄ and concentrated under reduced pressure. Flash chromatography (ISCO system, silica 24 g, 0-30% ethyl acetate in hexane) provided A-4-2 (608 mg, 1.78 mmol, 67%).

Step 2. To a solution of A-1-1 (100 mg, 588 µmol) in DMF (3.00 L) was added cesium carbonate (479 mg, 1.5 mmol) and A-4-2 (200 mg, 588 mol). The mixture was stirred at 70° C. for 17 hr. The reaction mixture was cooled, diluted with DCM (5 mL), filtered through a syringe filter and concentrated under reduced pressure. Flash column chromatography (12 g silica, ISCO, 0-80% ethyl acetate in hexane) gave A-4-3 (47 mg, 138 µmol, 23% yield).

Step 3. To A-4-3 (47 mg, 138 µmol) in anhydrous THF (3.9 mL) at 0° C. was added LiBH₄ (9 mg, 415 µmol). The reaction was warmed to 22° C. and stirred for 21 hrs. The reaction was cooled to 0° C. and quenched with and 2 M NaOH (3 mL) and water (3 mL) then extracted with DCM (3×5 mL). The combined organic layer was washed with brine and dried over sodium sulfate and concentrated under reduced pressure. Flash column chromatography (12 g silica, ISCO, 0-12.5% methanol in dichloromethane) provided A-4-4 (37.1 mg, 119 µmol, 86% yield).

Step 4. To A-4-4 (37.1 mg, 120 µmol) in DCM (1 mL) was added mesyl chloride (20.5 mg, 179 µmol, 14 uL). The reaction was cooled to 0° C. and Hunig's base (46 mg, 357 µmol, 62 µL) was added. The reaction was slowly warmed to 22° C. and stirred for 71 hr. The reaction was cooled to −20° C. and quenched with 2 M HCl (aq) (2 mL). Diluted with water and DCM (2 mL each), layers were partitioned, and the aqueous layer was extracted DCM (2×5 mL). The combined organic layer was washed with brine and dried over sodium sulfate. Flash column chromatography (12 g silica, ISCO, 0-40% ethyl acetate in hexane) to afford A-4 (25.2 mg, 75.9 μmol, 75% yield).

| Cpd# | Structure (R = OMs, Cl) | MS [M + Na] m/z |
|---|---|---|
| A-1 | F—⌬—O—C(CH3)2—CH2—NHBoc (with CH2R) | 354.1 |
| A-2 | F—⌬—O—CH2—cyclopropyl-CH2—NHBoc | 366.1 |
| A-3 | F—⌬—O—CH2CH2CH2—NHBoc | 340.1 |
| A-4 | F—⌬—O—CH2—cyclopropyl—NHBoc | 352.1 |
| A-5 | F—⌬—O—CH2CH2—CH(CH3)—NHBoc | 354.1 |
| A-6 | F—⌬—O—CH2CH2—cyclopropyl—CH2NHBoc | 366.1 |
| A-7 | F—⌬—O—CH2—C(CH3)2—CH2NHBoc | 368.2 |
| A-8 | F—⌬—O—CH2CH2—cyclopropyl—NHBoc | |

Example 4: General Method D

Preparation of ethyl 5-chloro-6-hydroxy-pyrazolo[1,5-a]pyrimidine-3-carboxylate (B)

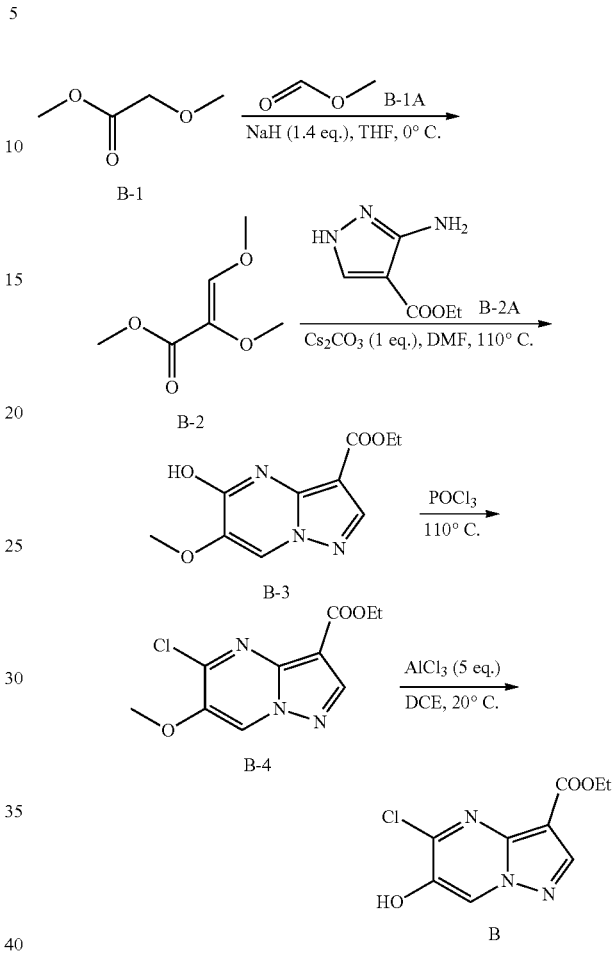

Step 1. To a solution of B-1 (150 g, 1.44 mol, 143 mL, 1.00 eq.) and B-1A (104 g, 1.73 mol, 105 mL, 1.20 eq.) in tetrahydrofuran (3.00 L) was added sodium hydride (80.7 g, 2.02 mol, 60.0% purity, 1.40 eq.) slowly at 0° C. over a period of 30 minutes under nitrogen. During which the temperature was maintained below 0° C. The reaction mixture was stirred at 0° C. for 12 hr. The formation of white solids was observed, methyl tert-butyl ether (2.00 L) was added, filtered, and the filtered cake was dried under reduced pressure to give the crude B-2 (283 g, crude) as light-yellow solid.

Step 2. To a solution of B-2A (165 g, 1.06 mol, 1.00 eq.) in DMF (3.00 L) was added cesium carbonate (624 g, 1.91 mol, 1.80 eq.) and B-2 (279 g, 1.91 mol, 1.80 eq.). The mixture was stirred at 110° C. for 12 hr. The reaction mixture was diluted with water (3.00 L), hydrochloric acid (5.00 M, 1.80 L) was added to the mixture slowly at 20° C., and the resulting precipitated solids was filtered and washed with methyl alcohol (300 mL). The filtered cake was concentrated under reduced pressure to give the crude B-3 (162 g, 609 mmol, 57.4% yield, 89.3% purity) as yellow solid.

Step 3. B-3 (100 g, 375 mmol, 1.00 eq.) was added into phosphorus oxychloride (300 mL). The mixture was stirred at 110° C. for 12 hr. The reaction mixture was concentrated under reduced pressure to remove solvent and until product precipitated. The residue was diluted with ice water (1.00 L)

and filtered to remove the solvent. Then the filter cake was dissolved in dichloromethane (2.00 L) and water (2.00 L) was added. The organic phase was separated, washed with brine (300 mL), dried over anhydrous sodium sulfate, filtered and concentrated under reduced pressure to give B-4 (64.0 g, 213 mmol, 56.7% yield, 85.0% purity) as gray solid.

Step 4. Aluminum trichloride (752 g, 5.64 mol, 308 mL, 5.00 eq.) was added in one portion to anhydrous dichloroethane (4.90 L) and the mixture was stirred under nitrogen at 20° C. for 10 minutes, then B-4 (324 g, 1.13 mol, 1.00 eq.) was added to the mixture in five equal portions. The mixture was stirred at 20° C. for 24 hr. The reaction mixture was quenched by addition of hydrochloric acid (5.00 M, 2.00 L) at 0° C., diluted with water (1.00 L), and then extracted with ethyl acetate (3.00 L×3). The combined organic layers were washed with water (2.00 L) and brine (1.00 L×2), dried over anhydrous sodium sulfate, filtered and concentrated under reduced pressure to give the crude product B (280 g, 920 mmol, 81.6% yield, 79.4% purity) as gray solid.

Example 5: General Method E

Preparation of Compound ethyl (3S)-3-(difluoromethyl)-3,4-dihydro-2H-pyrazolo[1,2]pyrimido[2,4-d][1,4]oxazine-6-carboxylate (C)

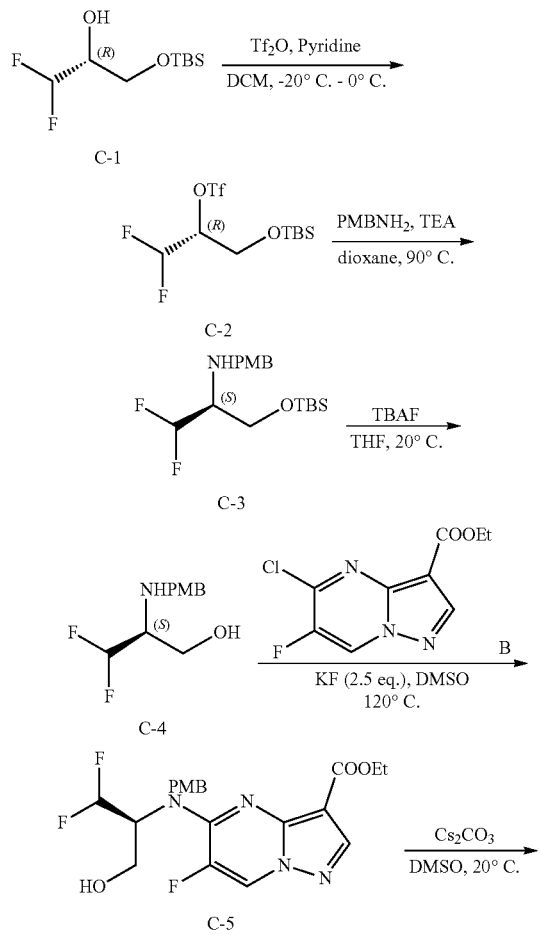

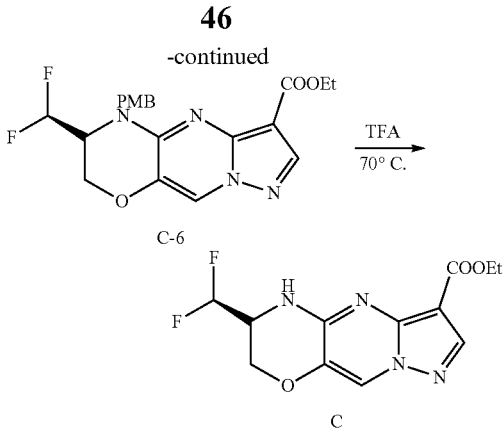

Step 1: To a solution of C-1 (5.00 g, 22.1 mmol, 1.00 eq.) in DCM (120 mL) was added pyridine (2.80 g, 35.4 mmol, 2.85 mL, 1.60 eq.) and trifluoroacetic anhydride (7.48 g, 26.5 mmol, 4.37 mL, 1.20 eq.) at −20° C. The mixture was stirred at −20° C.-0° C. for 5 hr. The reaction mixture was concentrated under reduced pressure to remove solvent at 30° C. The residue was diluted with water (50.0 mL) and extracted with Petroleum ether/Ethyl acetate=10:1 (50.0 mL×3). The combined organic layers were washed with brine (30.0 mL), dried over anhydrous sodium sulfate, filtered and concentrated under reduced pressure to give a residue. The residue was purified by column chromatography (SiO$_2$, Petroleum ether/Ethyl acetate=1/0 to 50/1) to give C-2 (6.70 g, 16.8 mmol, 76.2% yield, 90.0% purity) as a light-yellow oil.

Step 2. To a solution of C-2 (0.50 g, 1.40 mmol, 1.00 eq.) in dioxane (5.00 mL) was added (4-methoxyphenyl)methanamine (229 mg, 1.67 mmol, 216 μL, 1.20 eq.) and triethylamine (169 mg, 1.67 mmol, 233 μL, 1.20 eq.). The mixture was stirred at 90° C. for 12 hrs. The reaction mixture was diluted with water (30.0 mL) and extracted with ethyl acetate (20.0 mL×2). The combined organic layers were washed with brine (15.0 mL), dried over anhydrous sodium sulfate, filtered and concentrated under reduced pressure to give a residue. The residue was purified by column chromatography (SiO$_2$, Petroleum ether/Ethyl acetate=50/1 to 10/1) to give C-3 (0.35 g, 1.01 mmol, 72.3% yield, 99.5% purity) as a light-yellow oil.

Step 3. To a solution of C-3 (3.35 g, 9.70 mmol, 1.00 eq.) in tetrahydrofuran (34.0 mL) was added a solution of tetrabutyl ammonium fluoride in tetrahydrofuran (1.00 M, 9.70 mL, 1.00 eq.). The mixture was stirred at 20° C. for 2 hr. The reaction mixture was quenched by water (80.0 mL) at 20° C. and extracted with ethyl acetate (50.0 mL×2). The combined organic layers were washed with brine (50.0 mL), dried over anhydrous sodium sulfate, filtered and concentrated under reduced pressure to give a residue. The residue was purified by column chromatography (SiO$_2$, Petroleum ether/Ethyl acetate=30/1 to 10/1) to give C-4 (2.10 g, 8.99 mmol, 92.7% yield, 99.0% purity) as a light-yellow oil.

Step 4. To a solution of C-4 (2.60 g, 11.2 mmol, 1.00 eq.) in dimethyl sulfoxide (50.0 mL) was added potassium fluoride (1.63 g, 28.1 mmol, 658 μL, 2.50 eq.) and B (2.74 g, 11.2 mmol, 1.00 eq.). The mixture was stirred at 120° C. for 3 hr. The reaction mixture was diluted with water (300 mL) and extracted with ethyl acetate (50.0 mL×3). The combined organic layers were washed with brine (50.0 mL×3), dried over anhydrous sodium sulfate, filtered and concentrated under reduced pressure to give a residue. The residue was purified by column chromatography (SiO$_2$, Petroleum ether/Ethyl acetate=10/1 to 2/1) to give compound C-5 (1.00 g, 1.83 mmol, 16.3% yield, 80.3% purity) as a yellow oil.

Step 5. To a solution of C-5 (1.00 g, 2.28 mmol, 1.00 eq.) in dimethyl sulfoxide (70.0 mL) was added cesium carbonate (2.97 g, 9.12 mmol, 4.00 eq.). The mixture was stirred at 25° C. for 2 hr. The reaction mixture was diluted with water (300 mL) and extracted with ethyl acetate (50.0 mL×3). The combined organic layers were washed with brine (100 mL×3), dried over anhydrous sodium sulfate, filtered and concentrated under reduced pressure to give C-6 (0.75 g, 1.43 mmol, 62.9% yield, 80.0% purity) as a yellow solid.

Step 6. C-6 (0.51 g, 1.22 mmol, 1.00 eq.) was added into trifluoroacetic acid (10.0 mL). The mixture was stirred at 70° C. for 4 hr. The reaction mixture was concentrated under reduced pressure to give a residue. The residue was purified by column chromatography (SiO$_2$, Petroleum ether/Ethyl acetate=10/1 to 1/1) to give C (0.27 g, 862 µmol, 70.8% yield, 96.0% purity) as a gray solid.

Example 6: General Method F

Preparation of (4S)-4-(Difluoromethyl)-8-fluoro-13,13-dimethyl-3,4,13,14-tetrahydro-6H-18,1-(metheno)[1,4]oxazino[3,4-i]pyrazolo[4,3-f][1,4,8,10]benzoxatriazacyclotridecin-15(12H)-one (1)

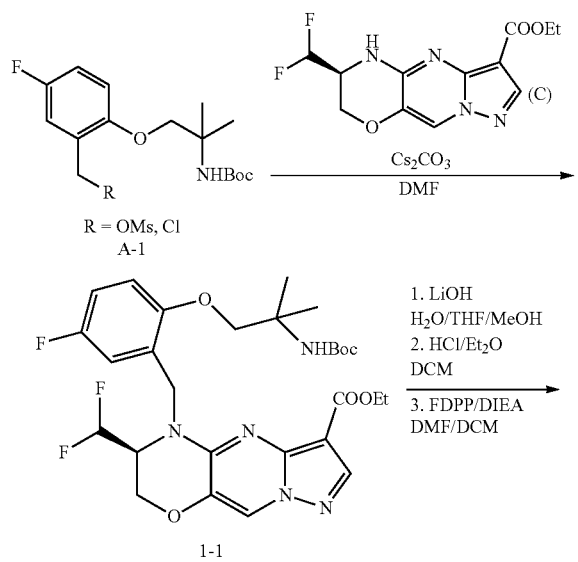

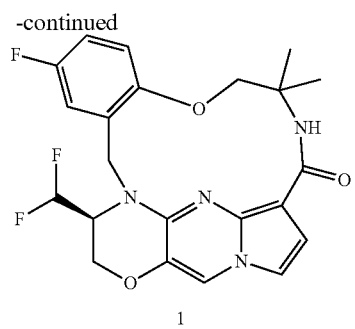

Step 1: A-1 (R=Cl, 25.2 mg, 75.95 µmol) was dissolved in DMF (0.5 mL) at room temperature. Cs$_2$CO$_3$ (65.55 mg, 201.18 µmol) was added followed by C (20 mg, 67.06 µmol). The mixture stirred at 22° C. for 18 hr. Reaction was diluted with DCM (5 mL) and cooled. The solution was filtered, and the filtrate was concentrated under reduced pressure. Flash column chromatography (ISCO, 12 g, 20-80% ethyl acetate in hexanes) to afford 1-1 (23.4 mg, 39.42 µmol, 59% yield).

Step 2: 1. To a solution of 1-1 (23.4 mg, 39.42 µmol) in THF (1 mL), 2 mL of Ethanol (2 mL) and Methanol (1 mL) at ambient temperature was added aqueous LiOH (2 M, 2 mL). The mixture was stirred at 22° C. for 36 hr. Cooled to 20° C. then quenched with aqueous HCl solution (2.0 M, 2.1 mL) to acidic pH. The mixture was diluted with water (10 mL), and extracted with DCM (3×10 mL). The combined organic layer was washed with brine and then dried over Na$_2$SO$_4$. Salts were filtered and the filtrate was concentrated under reduced pressure and dried under high vacuum. The crude was used directly without further purification and assuming quantitative yield. 2. Crude was dissolved in anhydrous DCM (2 mL) and HCl/4 M DIOXANE (4 M, 2 mL) was added. The mixture was stirred for 45 min at 22° C., then concentrated to dryness under reduced pressure followed by high vacuum treatment. The obtained crude was used directly without further purification assuming quantitative yield. 3. Anhydrous DCM (1.90 mL) was added to the crude followed by Hunig's base (50.93 mg, 394.05 µmol, 68.64 uL) and FDPP (22.71 mg, 59.11 µmol) in one portion. The reaction mixture was allowed to stir for 18 hr then quenched reaction with 2 M Na$_2$CO$_3$ solution (5 mL). Mixture was stirred for 5 min then extracted with DCM (3×10 mL). Combined organic extracts were dried with Na$_2$SO$_4$ and concentrated under reduced pressure. Flash chromatography (ISCO system, silica 12 g, 0-10% methanol in dichloromethane) provided compound 1 (10.8 mg, 24.14 µmol, 61.26% yield, 3 steps).

Compounds 2 through 8 were prepared according to General Method F with starting materials A-2 through A-8, respectively, with compound B.

| Cpd | Structure | MS [M + H] m/z | $^1$H NMR (DMSO-d$_6$) δ ppm |
|---|---|---|---|
| 1 | 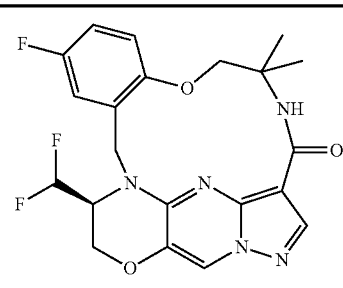 | 448.17 | (500 MHz) 9.14 (s, 1 H) 8.66 (s, 1 H) 8.00 (s, 1 H) 7.49 (dd, J = 9.16, 2.86 Hz, 1 H) 7.00-7.16 (m, 2 H) 6.36-6.64 (m, 1 H) 5.60 (d, J = 14.89 Hz, 1 H) 5.04 (br t, J = 10.02 Hz, 1 H) 4.67 (d, J = 12.03 Hz, 1 H) 4.34-4.41 (m, 1 H) 4.30 (d, J = 14.89 Hz, 1 H) 4.09 (d, J = 9.74 Hz, 1 H) 3.88 (d, J = 9.74 Hz, 1 H) 1.63 (s, 3 H) 1.48 (s, 3 H) |

-continued

| Cpd | Structure | MS [M + H] m/z | $^1$H NMR (DMSO-d$_6$) δ ppm |
|---|---|---|---|
| 2 | 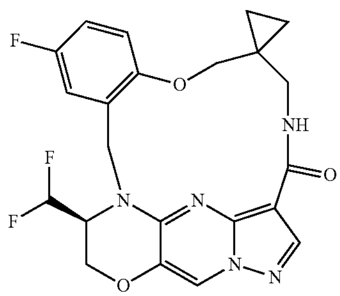 [SMILES: O=C1NCC2(CC2)COc2ccc(F)cc2CN2c3nc4c1cnn4cc3OC[C@H]2C(F)F] | 460.17 | (500 MHz) 8.65 (s, 1 H) 8.40-8.48 (m, 1 H) 8.06 (s, 1 H) 7.36 (br d, J = 9.16 Hz, 1 H) 6.98-7.07 (m, 2 H) 6.50 (td, J = 54.70, 4.01 Hz, 1 H) 5.71 (br d, J = 14.89 Hz, 1 H) 4.93-5.03 (m, 1 H) 4.78 (d, J = 10.31 Hz, 1 H) 4.66 (d, J = 12.03 Hz, 1 H) 4.34-4.43 (m, 1 H) 4.25 (d, J = 15.47 Hz, 1 H) 3.76-3.83 (m, 1 H) 3.46 (br d, J = 10.31 Hz, 1 H) 2.82 (br dd, J = 13.75, 2.86 Hz, 1 H) 0.81-0.89 (m, 1 H) 0.65-0.76 (m, 3 H) |
| 3 | 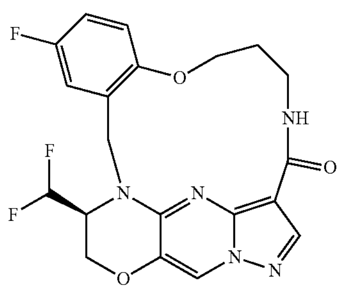 [SMILES: O=C1NCCCOc2ccc(F)cc2CN2c3nc4c1cnn4cc3OC[C@H]2C(F)F] | 434.19 | (500 MHz) 8.65 (s, 1 H) 8.23 (br d, J = 4.01 Hz, 1 H) 8.06 (s, 1 H) 7.32 (br d, J = 8.59 Hz, 1 H) 7.02-7.06 (m, 2 H) 6.35-6.61 (m, 1 H) 5.62 (d, J = 14.32 Hz, 1 H) 4.91-5.00 (m, 1 H) 4.67 (d, J = 12.03 Hz, 1 H) 4.40 (br dd, J = 10.88, 5.16 Hz, 2 H) 4.20-4.29 (m, 2 H) 3.62-3.71 (m, 1 H) 3.37-3.43 (m, 1 H) 2.03-2.16 (m, 2 H) |
| 4 | 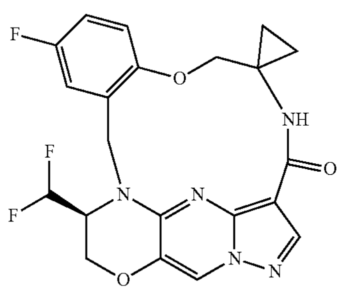 [SMILES: O=C1NC2(CC2)COc2ccc(F)cc2CN2c3nc4c1cnn4cc3OC[C@H]2C(F)F] | 446.09 | (500 MHz) 9.09 (s, 1 H) 8.66 (s, 1 H) 7.99 (s, 1 H) 7.40 (dd, J = 9.45, 3.15 Hz, 1 H) 7.04 (td, J = 8.45, 3.15 Hz, 1 H) 6.92-6.98 (m, 1 H) 6.50 (td, J = 54.84, 3.72 Hz, 1 H) 5.62 (d, J = 14.32 Hz, 1 H) 4.96-5.04 (m, 1 H) 4.68 (d, J = 12.03 Hz, 1 H) 4.32-4.38 (m, 1 H) 4.21-4.31 (m, 2 H) 3.91 (d, J = 10.31 Hz, 1 H) 1.89-1.96 (m, 1 H) 0.95-1.07 (m, 2 H) 0.73-0.80 (m, 1 H) |
| 5 | 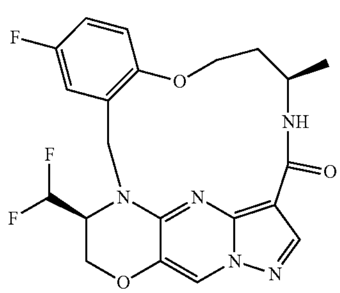 [SMILES: C[C@@H]1CCOc2ccc(F)cc2CN2c3nc4c(cnn4cc3OC[C@H]2C(F)F)C(=O)N1] | 448.20 | (300 MHz) 8.63 (s, 1 H) 8.21 (d, J = 6.51 Hz, 1 H) 8.05 (s, 1 H) 7.31 (dd, J = 9.17, 2.75 Hz, 1 H) 6.92-7.07 (m, 2 H) 6.26-6.68 (m, 1 H) 5.62 (d, J = 14.76 Hz, 1 H) 4.89-5.02 (m, 1 H) 4.66 (d, J = 12.10 Hz, 1 H) 4.35 (br dd, J = 11.83, 2.75 Hz, 1 H) 4.08-4.28 (m, 4 H) 2.16-2.30 (m, 1 H) 1.87-2.02 (m, 1 H) 1.26 (d, J = 6.24 Hz, 3 H) |
| 6 | 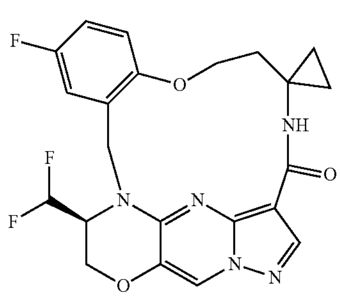 [SMILES: O=C1NC2(CCOc3ccc(F)cc3CN3c4nc5c1cnn5cc4OC[C@H]3C(F)F)CC2] | 460.20 | (500 MHz) 8.62 (s, 1 H) 8.18 (s, 1 H) 7.96 (s, 1 H) 7.24 (dd, J = 9.16, 2.86 Hz, 1 H) 7.07 (dd, J = 9.16, 4.58 Hz, 1 H) 6.96-7.03 (m, 1 H) 6.49 (td, J = 54.56, 3.72 Hz, 1 H) 5.58 (br d, J = 14.89 Hz, 1 H) 4.88-4.95 (m, 1 H) 4.66 (d, J = 12.03 Hz, 1 H) 4.36-4.54 (m, 2 H) 4.20-4.34 (m, 2 H) 2.09-2.22 (m, 1 H) 1.57-1.75 (m, 2 H) 1.12-1.17 (m, 1 H) 0.75-0.84 (m, 1 H) 0.66-0.73 (m, 1 H) |

| Cpd | Structure | MS [M + H] m/z | $^1$H NMR (DMSO-d$_6$) δ ppm |
|---|---|---|---|
| 7 | 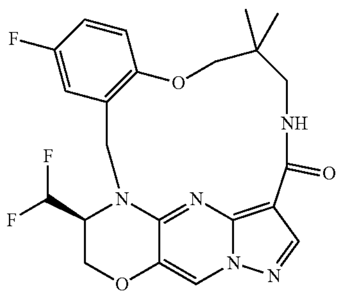 [SMILES: CC1(C)CNC(=O)c2cnn3cc4c(nc23)N(Cc2cc(F)ccc2OC1)[C@H](C(F)F)CO4] | 462.17 | (300 MHz) 8.64 (s, 1 H) 8.46 (br d, J = 3.21 Hz, 1 H) 8.07 (s, 1 H) 7.40 (dd, J = 9.31, 2.89 Hz, 1 H) 7.01-7.17 (m, 2 H) 6.27-6.70 (m, 1 H) 5.66 (d, J = 15.22 Hz, 1 H) 4.92-5.07 (m, 1 H) 4.66 (d, J = 12.10 Hz, 1 H) 4.23-4.42 (m, 3 H) 3.60-3.68 (m, 1 H) 3.35-3.42 (m, 1 H) 3.22 (s, 1 H) 1.26 (s, 3 H) 1.04 (s, 3 H) |
| 8 | 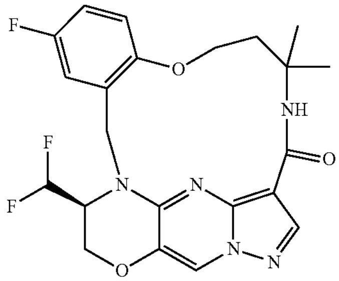 [SMILES: CC1(C)CCOc2ccc(F)cc2CN2c3nc4c(cnn4cc3OC[C@H]2C(F)F)C(=O)N1] | 462.22 | (500 MHz) 8.61 (s, 1 H) 7.98-8.08 (m, 2 H) 7.41 (dd, J = 9.16, 2.86 Hz, 1 H) 7.02-7.14 (m, 2 H) 6.46 (td, J = 54.56, 3.72 Hz, 1 H) 5.70 (br d, J = 14.89 Hz, 1 H) 5.01 (br d, J = 12.60 Hz, 1 H) 4.64 (d, J = 12.03 Hz, 1 H) 4.49 (br t, J = 10.02 Hz, 1 H) 4.29 (br d, J = 10.31 Hz, 1 H) 4.21 (br d, J = 14.89 Hz, 1 H) 3.95 (br dd, J = 9.45, 5.44 Hz, 1 H) 2.25 (br dd, J = 15.46, 9.74 Hz, 1 H) 1.87 (br dd, J = 15.46, 5.15 Hz, 1 H) 1.59 (s, 3 H) 1.52 (s, 3 H) |

Example 7: Biologic Assays

In-Vitro Assays
Materials and Methods
Biochemical Kinase Assay Method

The biochemical kinase assay was performed at Reaction Biology Corporation (Malvern, Pa.) following the procedures described in the reference (Anastassiadis T, et al *Nat Biotechnol.* 2011, 29, 1039). Specific kinase/substrate pairs along with required cofactors were prepared in reaction buffer; 20 mM Hepes pH 7.5, 10 mM MgCl$_2$, 1 mM EGTA, 0.02% Brij35, 0.02 mg/ml BSA, 0.1 mM Na$_3$VO$_4$, 2 mM DTT, 1% DMSO. Compounds were delivered into the reaction, followed about 20 min later by addition of a mixture of ATP (Sigma, St. Louis Mo.) and $^{33}$P ATP (Perkin Elmer, Waltham Mass.) to a final concentration of 10 μM. Reactions were carried out at room temperature for 120 min, followed by spotting of the reactions onto P81 ion exchange filter paper (Whatman Inc., Piscataway, N.J.). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. IC$_{50}$ values and curve fits were obtained using Prism (GraphPad Software).

Cell Lines and Cell Culture:

Colorectal cell line KM 12 (harboring endogenous TPM3-TRKA fusion gene) was obtained from NCI. Acute myelogenous cell line KG-1 (harboring endogenous OP2-FGFR1 fusion gene) was purchased from ATCC.

Cloning and Ba/F3 Stable Cell Lines Creation

The EML4-ALK gene (variant 1) wild type, G1202R, G1202R/L1196M, G1202R/L1198F, G1202R/C1156Y, and L1196M/L1198F were synthesized at GenScript and cloned into pCDH-CMV-MCS-EF1-Puro plasmid (System Biosciences, Inc). Ba/F3 EML4-ALK wild type, G1202R, G1202R/L1196M, G1202R/L1198F, G1202R/C1156Y, L1196M/L1198F, L1198F/C1156Y, G1202R/G1269A, and G1202R/G1269A/L1204V were generated by transducing Ba/F3 cells with lentivirus containing EML4-ALK wide type, G1202R, G1202R/L1196M, G1202R/L1198F, G1202R/C1156Y, L1196M/L1198F L1198F/C1156Y, G1202R/G1269A, or G1202R/G1269A/L1204V. Stable cell lines were selected by puromycin treatment, followed by IL-3 withdrawal. Briefly, 5×10$^6$ Ba/F3 cells were transduced with lentivirus supernatant in the presence of 8 μg/mL protamine sulfate. The transduced cells were subsequently selected with 1 μg/mL puromycin in the presence of IL3-containing medium RPMI1640, plus 10% FBS. After 10-12 days of selection, the surviving cells were further selected for IL3 independent growth.

Cell Proliferation Assays:

Two thousand cells per well were seeded in 384 well white plate for 24 hrs, and then treated with compounds for 72 hr (37° C., 5% CO2). Cell proliferation was measured using CellTiter-Glo luciferase-based ATP detection assay (Promega) following the manufactures's protocol. IC$_{50}$ determinations were performed using GraphPad Prism software (GraphPad, Inc., San Diego, Calif.).

Immunoblotting for Cellular Kinase Phosphorylation Assays

Half a million cells (Ba/F3 EML4-ALK WT or G1202R) per well were seeded in 24 well plate for 24 hr, and then treated with compound for 4 hr. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1× Halt protease and phosphatase inhibitors (Thermo Scientific). Protein lysates (approximately 20 μg) was resolved on 4-12% Bolt Bis-Tris precasted gels with MES running buffer (Life Technologies), transferred to nitrocellulose membranes using Trans-Blot Turbo Transfer System (Bio-Rad) and detected with antibodies targeting phosphorylated ALK (Y1282/1283) (Cell Signaling Technology), ALK (Y1604), total ALK (Cell Signaling Technology), Actin (Cell Signaling Technology). Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences). The relative density of the chemiluminescent bands was quantified via Image Studio Digits from LICOR.

Solubility Test

Aliquot of 1.035 mL phosphate buffer (PB) (pH 7.4) was added into 2.07 mg of the test compound (for a 2 mg·mL$^{-1}$ upper limiting solubility determination) in a 1.5 mL tubes. The mixture was ultrasonically treated for 10 min and rotated on rotator at room temperature for more than 8 hr. After rotation, the tube was ultrasonically treated for 10 min and centrifuged at 13000 rpm for 15 min. 0.3 mL of the supernatant was transferred into a 0.6 mL tube and discarded after rotated for 5 min for rinsing, then about 0.6 mL of the residual supernatant was transferred into the rinsed tube and centrifuged again at 13000 rpm for 15 min. The supernatant after every centrifugation was appropriately diluted and transferred for LC-MS/MS analysis where a standard curve was constructed with 7 concentration levels (2, 4, 10, 20, 40, 100 and 200 μg mL$^{-1}$) and used for the quantitation of the analyte in PB.

Liver Microsomal Stability Studies

1. Preparation of Stock and Working Solution

The test compound stock solution was prepared by weighing 1.07 mg and dissolving in 0.261 mL of DMSO to achieve the concentration of 10 mM. Working solution of the test compound was prepared by diluting stock solution using DMSO to yield the concentration of 300 μM.

2. Incubation

The assay was carried out in 96-well microtiter plates. In each well, the reaction mixture (25 μL) contained the test compound at the final concentration of 1 μM, 0.5 mg/mL liver microsome protein, and 1 mM NADPH in 100 mM potassium phosphate, pH 7.4 buffer with 3.3 mM MgCl$_2$. The mixtures were incubated in duplicate at 37° C. for 0, 15, 30 or 60 minutes, and 150 μL of quench solution (acetonitrile with 0.1% formic acid) with internal standard (bucetin for positive ESI mode) was added into each well of reaction to terminate the reaction. The plates were then sealed and centrifuged at 4° C. for 15 minutes at 4000 rpm. The resulting supernatant was transferred to fresh plates for LC-MS/MS analysis of the test compounds. Verapamil was used as the positive control to validate the assay system.

3. LC-MS/MS Analysis

All samples were analyzed with LC-MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in acetonitrile (solvent B).

4. Calculation

The extent of metabolism was calculated based on the disappearance of the test compound, compared to its initial concentration. The initial rates of clearance of test compounds were calculated using linear regression plot of semi-log % remaining of compounds versus time. The elimination rate constant (equals to negative slope) of the linear regression plot was then used to determine t112 and the intrinsic clearance ($CL_{Int}$) using the following formula:

$$k = -\text{slope}$$

$$t_{1/2} = 0.693/k$$

$$CL_{int} = k/C_{protein}$$

Where $C_{protein}$ (mg/mL) is the microsomal protein concentration in the incubation system. This method of intrinsic clearance determination makes the assumption that the test compound concentration is far below the Michaelis-Menten constant of the compound to its metabolizing enzymes.

In-Vivo Studies

Subcutaneous Xenograft Models in Immune Compromised Mice

Female SCID/Beige mice (5-8 weeks of age) were obtained from Charles River Laboratory and were housed in Innovive IVC disposable cages on HEPA filtered ventilated racks with ad libitum access to rodent chow and water. About five million cells in 100 μL serum-free medium supplemented with 50% matrigel (Corning, Inc) were implanted subcutaneously in the right flank region of the mouse. Tumor size and body weight were measured on designated days. Tumor size was measured with an electronic caliper and tumor volume was calculated as the product of length*width$^2$*0.5. Mice were randomized by tumor size into treatment groups when tumor volume reached about 100-200 mm$^3$. Compound 1 or 2 was administered orally at pre-determined schemes and doses. Vehicle was used as negative control. Lorlatinib was used as a reference for efficacy evaluation. Tumor growth inhibition (TGI) was calculated as follows: If $TV_t > TV_0$, TGI=100%× $(1-(TV_t-TV_0)/(CV_t-CV_0))$; If $TV_t < TV_0$, TGI=100%×(2- $TV_t/TV_0$); where $TV_0$ was the mean tumor volume in the treatment group at the beginning of the treatment, $TV_t$ was the mean tumor volume in the treatment group at the end of the treatment, $CV_0$ was the mean tumor volume in the vehicle control group at the beginning of the treatment, and $CV_t$ was the mean tumor volume in the vehicle control group at the end of the treatment. A TGI that is larger than 100% indicates tumor regression. Statistical analyses were performed using GraphPad Prism 8.4.0 and p<0.05 was considered as statistically significant difference.

Tumor Processing and Immunoblotting for In Vivo Pharmacodynamic Studies

Mice bearing xenograft tumors were humanely euthanized and tumors were resected and snap frozen in liquid nitrogen and stored at −80° C. Frozen tumor samples were processed at 4° C. in 1× Cell Lysis Buffer (Cell Signaling Technologies) to extract proteins. SDS loading samples were prepared by addition of 4×LDS Sample Buffer and 10× Reducing Reagent (Life Technologies, Inc) to protein lysate. Tumor SDS protein samples were processed by SDS-PAGE and immunoblotted with rabbit anti-phosphorylated ALK Y1282/1283, rabbit anti-phosphorylated ALK Y1604, rabbit anti-ALK and mouse anti-actin antibodies (Cell Signaling Technologies). The signals from immunoblot were detected by C-DiGit Blot Scanner from LI-COR and the signal intensity were quantified using the Image Studio Digit software (LI-COR).

Mouse Pharmacokinetic Studies

Preparation of the Vehicle Solution for the Test Article

To prepare 1 L of the vehicle solution (0.5% CMC and 1.0% Tween 80), 10 g of Tween 80 was mixed with 985 mL of water into a 1 L bottle. The mixture was stirred until Tween 80 was completely dissolved. With continued stirring, 5 g of CMC was very slowly sprinkled into the solution. Stirring was continued until all CMC was dissolved, which might take several hr. The resulting vehicle solution was stored at 4° C.

PK Blood Sample Processing and Bioanalysis Procedure

The compound was suspended in the vehicle solution and the mice were orally administrated with a single dose of the compound at the selected dose level. The blood samples were collected according to the defined time table into tubes containing K2-EDTA, followed by gentle mixing to assure distribution of the anti-coagulant. Immediately after the blood sample was collected and mixed, it was placed on ice. The samples were then centrifuged at 4° C. for 10 minutes at 5,000 RPM. The plasma was harvested into pre-labeled tubes and stored at −80° C. until analyzed by LC-MS/MS.

In-Vitro Results

Enzymatic Kinase Activities Against ALK and Mutant ALKs

Compounds were tested against ALK and mutant ALKs in the enzymatic kinase catalytic activity assays at Reaction Biology Corporation. The results were reported in Table 1. Compound 1 ("Cpd 1") and Compound 2 ("Cpd 2") each showed potent kinase inhibitory activities on ALK and mutant ALKs with $IC_{50}$s <10 nM.

TABLE 1

| Kinase | Cpd 1 $IC_{50}$ (nM) | Cpd 2 $IC_{50}$ (nM) |
|---|---|---|
| ALK | 1.43 | 1.40 |
| ALK (C1156Y) | 0.19 | 0.11 |
| ALK (D1203N) | 4.36 | 2.90 |
| ALK (delete G1202) | 0.53 | 0.45 |
| ALK (E1210K) | 0.34 | 0.21 |
| ALK (E1210K/D1203N) | 6.29 | 4.00 |
| ALK (E1210K/S1206C) | 0.22 | 0.13 |
| ALK (F1174C) | 1.78 | 0.92 |
| ALK (F1174L) | 0.69 | 0.42 |
| ALK (F1174S) | 1.20 | 0.76 |
| ALK (F1245C) | 0.75 | 0.41 |
| ALK (G1202R) | 0.88 | 0.74 |
| ALK (G1269A) | 1.55 | 1.28 |
| ALK (G1269S) | 6.60 | 6.14 |
| ALK (I1171N) | 2.29 | 1.16 |
| ALK (L1152P) | 2.92 | 1.96 |
| ALK (L1152R) | 1.10 | 0.83 |
| ALK (L1196M) | 0.29 | 0.18 |
| ALK (L1198F) | 1.05 | 0.85 |
| ALK (L1198F/C1156Y) | 0.24 | 0.15 |
| ALK (L1198F/G1202R) | 0.63 | 0.49 |
| ALK (L1198F/L1196M) | 0.18 | 0.10 |
| ALK (R1275Q) | 0.82 | 0.72 |
| ALK (S1206R) | 0.50 | 0.31 |
| ALK (T1151-L1152insT) | 1.25 | 0.86 |
| ALK (T1151M) | 0.39 | 0.28 |
| ALK (V1180L) | 1.61 | 0.51 |

Anti-Cell Proliferation Activity

Compounds were tested in cell proliferation assays in Ba/F3 cells engineered with EML4-ALK and EML4-ALK G1202R, and also in KM12 cells having TPM3-TRKA fusion and KG-1 cells having OP2-FGFR1 fusion. The results were summarized in Table 2.

TABLE 2

| Cpd | BaF3 EML4-ALK $IC_{50}$ (nM) | BaF3 EML4-ALK G1202R $IC_{50}$ (nM) | KM12 (TPM3-TRKA) IC50 (nM) | KG-1 cell (OP2-FGFR1) $IC_{50}$ (nM) |
|---|---|---|---|---|
| 1 | 0.8 | 0.2 | <0.2 | 554.2 |
| 2 | <0.2 | 0.2 | <0.2 | 3.8 |
| 3 | 9.7 | 9.3 | <0.2 | 75.3 |
| 4 | 9 | 35.7 | N/A | 60.9 |
| 5 | 46.3 | NA | <0.2 | 513.5 |
| 6 | 27.7 | 152.9 | <0.2 | 385.3 |
| 7 | 22 | NA | <0.2 | 40.7 |
| 8 | 186 | 122.5 | <0.2 | 2095 |

Comparative Examples 1 and 2 were also evaluated for anti-cell proliferation activity. The results were summarized in Table 2-A.

TABLE 2-A

| Cpd | BaF3 EML4-ALK $IC_{50}$ (nM) | BaF3 EML4-ALK G1202R $IC_{50}$ (nM) | KM12 (TPM3-TRKA) $IC_{50}$ (nM) | KG-1 cell (OP2-FGFR1) $IC_{50}$ (nM) |
|---|---|---|---|---|
| Comp. Ex. 1 | 22.8 | 43.0 | <0.2 | 22.2 |
| Comp. Ex. 2 | <0.6 | <1 | 0.2 | 0.65 |

| Cpd | BaF3 JAK2 V617F $IC_{50}$ (nM) | BaF3 KIF5B-RET $IC_{50}$ (nM) | BaF3 KIF5B-RET G810R $IC_{50}$ (nM) | BaF3 KIF5B-RET V804M $IC_{50}$ (nM) | BaF3 TEL-TRKB $IC_{50}$ (nM) |
|---|---|---|---|---|---|
| Comp. Ex. 1 | 825 | 110 | 787 | 138 | 0.74 |
| Comp. Ex. 2 | 3450 | 180 | 1440 | 490 | <0.2 |

Anti-Cell Proliferation in Ba/F3 Cells Engineered with Mutant ALKs

Compounds were tested in cell proliferation assays in Ba/F3 cells engineered with EML4-ALK wildtype (WT) and mutant ALKs. The results were summarized in Table 3 and 3-A.

TABLE 3

| | Ba/F3 Cell Proliferation $IC_{50}$ (nM) | | | | | | | | |
|---|---|---|---|---|---|---|---|---|---|
| Cpd | ALK WT | ALK G1202R | ALK G1202R/ L1196M | ALK G1202R/ L1198F | ALK G1202R/ C1156Y | ALK L1196M/ L1198F | ALK L1198F/ C1156Y | ALK G1202R/ G1269A | ALK G1202R/ G1269A/ L1204V |
| 1 | 0.8 | 0.2 | 1.1 | <0.2 | <0.2 | <0.2 | <0.2 | 8.7 | 14.7 |
| 2 | <0.2 | 0.2 | 0.5 | <0.2 | <0.2 | <0.2 | | | |

A side-by-side comparison of Compound 1 with known kinase inhibitors in Ba/F3 cells engineered with EML4-ALK wildtype (WT) and mutant ALKs. is shown in Table 3-A.

TABLE 3-A

| EML4-ALK | Ba/F3 Cell proliferation IC$_{50}$ (nM) | | | | | |
|---|---|---|---|---|---|---|
| | Compound 1 | Crizotinib | Alectinib | Brigatinib | Ceritinib | Lorlatinib |
| WT | 0.4 | 50 | 7.4 | 12 | 3.9 | 0.8 |
| I1171N | 516 | 254 | 4310 | 49 | 72 | 48 |
| I1171S | 189 | 188 | 306 | 31 | 27 | 31 |
| I1171T | 316 | 232 | 210 | 33 | 29 | 25 |
| L1196M | 0.5 | 274 | 50.1 | 21.1 | 5.4 | 38.2 |
| L1198F | <0.2 | 18 | 397 | 74 | 618 | 30 |
| G1202R | 0.2 | 434 | 2690 | 188 | 329 | 52 |
| G1269A | 13 | 451 | 197 | 20 | 15 | 49 |
| G1269S | 701 | 1390 | 671 | 46 | 97 | 191 |
| L1196M/L1198F | <0.2 | 252 | 2250 | 253 | 1410 | 1310 |
| L1198F/C1156Y | <0.2 | 19.3 | 776 | 102 | 1310 | 140 |
| L1198F/I1171N | 1.6 | 626 | 236 | 55.1 | 64.1 | 78.7 |
| G1202R/C1156Y | 0.2 | 745 | 2420 | 810 | 1300 | 521 |
| G1202R/L1196M | 0.7 | 808 | >10000 | 1100 | 1260 | 4780 |
| G1202R/L1198F | <0.2 | 188 | 3000 | 2040 | 2010 | 1710 |
| G1202R/G1269A | 9.9 | 705 | 7200 | 164 | 303 | 636 |
| G1202R/G1269A/L1204V | 14.9 | 634 | 6740 | 176 | 345 | 673 |
| G1202R/G1269A/L1198F | 0.2 | 596 | >10000 | 907 | 1670 | 6330 |

Solubility

The solubility was tested at pH 7.4 and the results were summarized in Table 4.

TABLE 4

| Compound | Solubility (μg/mL) at pH 7.4 |
|---|---|
| Comp. Ex. 1 | 7.9 |
| Comp. Ex. 2 | 4.9 |
| Compound 1 | 3.3 |
| Compound 2 | 2.6 |

Liver Microsomal Stability

The liver microsomal stability was tested and the results were summarized in Table 5.

TABLE 5

| | Microsomal Stability Cl$_{int}$ (μL/min/mg) | | |
|---|---|---|---|
| Compound | Human (pooled) | Mouse (female) | Rat (female) |
| Comp. Ex. 1 | 2.6 | 22 | 10 |
| Comp. Ex. 2 | 3.9 | 21 | 5.9 |
| Compound 1 | 8.3 | 11 | 1.5 |
| Compound 2 | 8.8 | 25 | 3.5 |

In-Vivo Results

Mouse PK

The mouse PKs were determined and the results were summarized in Table 6.

TABLE 6

| Compound | C$_{max}$ (ng/mL) | T$_{max}$ (h) | AUC$_{all}$ (h * ng/mL) |
|---|---|---|---|
| Comp. Ex. 1 | 4190 | 0.5 | 12300 |
| Comp. Ex. 2 | 2900 | 0.5 | 18700 |
| Compound 1 | 1751 | 2.0 | 11900 |
| Compound 2 | 2510 | 2.0 | 14600 |

Effect of Compound 1 and 2 on Ba/F3 Cell-Derived Xenograft Tumors with the EML4-ALK G1202R Fusion SCID/Beige mice bearing Ba/F3 cell-derived tumors with the EML4-ALK G1202R fusion were randomized to seven groups with 8 mice per group on day 8 post inoculation and treated with vehicle BID, Compound 1 BID at 2 mg/kg, Compound 1 BID at 5 mg/kg, Compound 1 BID at 10 mg/kg, Compound 2 BID at 3 mg/kg, Compound 2 BID at 10 mg/kg and lorlatinib BID at 5 mg/kg, respectively. The tumor volume vs time data are shown as mean±sem in FIG. 1A. After 7 days of treatment, Compound 1 treatment inhibited tumor growth or led to tumor regression with TGIs of 64%, 120% and 200% at dose of 2, 5, and 10 mg/kg BID, respectively; in comparison, lorlatinib inhibited tumor growth with a TGI of 154% at 5 mg/kg BID. The statistical evaluation of Compound 1's effect on tumor volume included the vehicle treated group, Compound 1 treated groups at 2, 5, 10 mg/kg BID and the lorlatinib treated group, using mixed-effects model followed by post hoc Tukey's multiple comparisons test. The efficacy of Compound 1 on this model with EML4-ALK G1202R fusion started to be detectable on day 10 and the tumor volume in the groups treated with Compound 1 at all three dose levels is significantly smaller than that of the group treated with vehicle by the last day of treatment (on day 15, p=0.0007 for Compound 1 2 mg/kg vs vehicle and p<0.0001 for Compound 1 5 or 10 mg/kg vs vehicle). Compound 1 treatment at 10 mg/kg BID is more effective than treatment by lorlatinib at 5 mg/kg BID in this model with the EML4-ALK G1202R fusion, as indicated by significantly smaller tumor volume in the group treated with Compound 1 at 10 mg/kg BID than that of the group treated with lorlatinib on days 13, 14, 15 post inoculation (p<0.0001 on day 13 and 14, p=0.0003 on day 15).

Figure 1B:
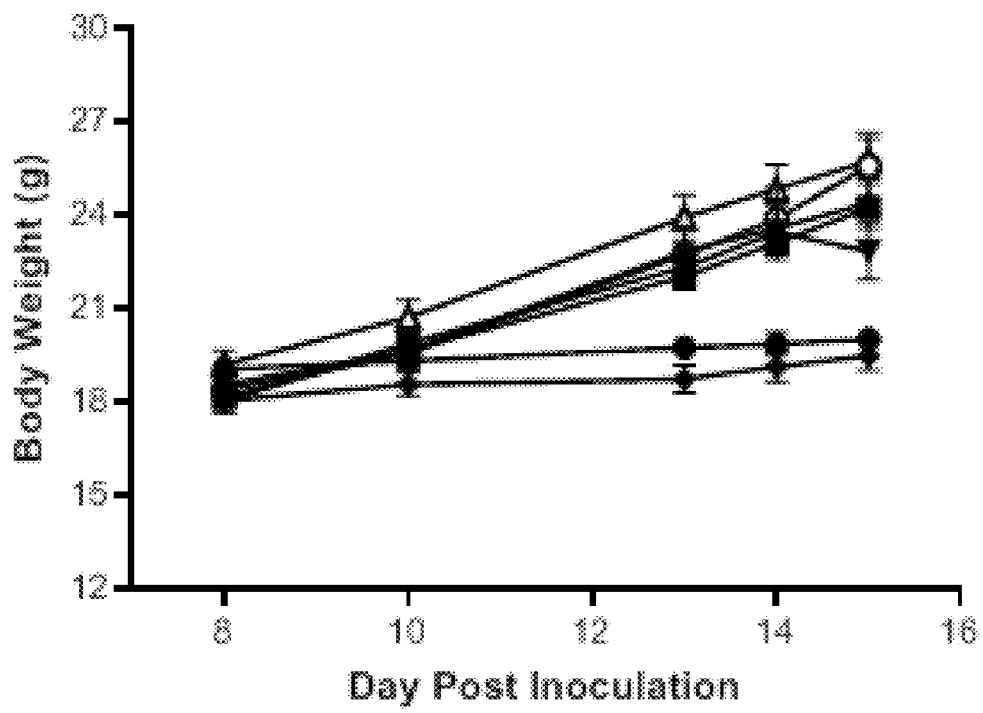
FIG. 1B shows body weights of mice bearing Ba/F3 cell derived xenograft tumors harboring an EML4-ALK fusion with a G1202R mutation. (●) vehicle; (■) Compound 1 (2 mg/kg BID); (▲) Compound 1 (5 mg/kg BID); (▼) Compound 1 (10 mg/kg BID); (○) Compound 2 (3 mg/kg BID); (Δ) Compound 2 (10 mg/kg BID); (♦) Lorlatinib (5 mg/kg).

The body weight vs time data are shown as mean±sem in FIG. 1B. There was no body weight loss in groups treated with Compound 1 at 2, 5, 10 mg/kg BID after 7 days of treatment. The statistical evaluation of Compound 1's effect on body weight included vehicle the treated group, Compound 1 treated groups at 2, 5, 10 mg/kg BID and the lorlatinib treated group, using mixed-effects model followed by post hoc Tukey's multiple comparisons test. The body weight in the group treated with Compound 1 at 2 mg/kg BID was significantly higher than that of the group treated with vehicle on days 13, 14, 15 post inoculation (p=0.0012 on day 13, p=0.0001 on day 14, p<0.0001 on day 15). The body weight in the group treated with Compound 1 at 5 mg/kg BID was significantly higher than that of the group treated with vehicle on days 13, 14, 15 post inoculation (p=0.0392 on day 13, p=0.0126 on day 14, p=0.0048 on day 15). The body weight in the group treated with Compound 1 at 10 mg/kg BID was significantly higher than that of the group treated with vehicle on days 13, 14 post inoculation (p=0.0495 on day 13, p=0.0250 on day 14).

After 7 days of treatment, Compound 2 treatment inhibited tumor growth with TGIs of 51% and 77% at dose of 3 and 10 mg/kg BID, respectively; whereas lorlatinib inhibited tumor growth with a TGI of 154% at 5 mg/kg BID. The statistical evaluation Compound 2's effect on tumor volume included the vehicle treated group, Compound 2 treated groups at 3 and 10 mg/kg BID and the lorlatinib treated group, using mixed-effects model followed by post hoc Tukey's multiple comparisons test. The effect of Compound 2 on tumor growth inhibition started to be detectable by day 13 at the 3 mg/kg dose level (p=0.0019 vs vehicle) and by day 10 at the 10 mg/kg dose level (p=0.0396 vs vehicle). On day 15, the last day of treatment, the tumor volume in the group treated with Compound 2 was significantly smaller than that of the group treated with vehicle (p=0.0272 for Compound 2 3 mg/kg vs vehicle; p=0.0052 for Compound 2 10 mg/kg vs vehicle).

There was no body weight loss in groups treated with Compound 2 at 3 and 10 mg/kg BID after 7 days of treatment. The statistical evaluation of Compound 2's effect on body weight included the vehicle treated group, Compound 2 treated groups at 3 and 10 mg/kg BID and the lorlatinib treated group, using mixed-effects model followed by post hoc Tukey's multiple comparisons test. The body weight in the group treated with Compound 2 at 3 mg/kg BID was significantly higher than that of the group treated with vehicle on days 13, 14, 15 post inoculation (p=0.0282 on day 13, p=0.0229 on day 14, p=0.0043 on day 15). The body weight in the group treated with Compound 2 at 10 mg/kg BID was significantly higher than that of the group treated with vehicle on days 13, 14, 15 post inoculation (p=0.0017 on day 13, p=0.0009 on day 14; p=0.0003 on day 15).

Figure 2A:
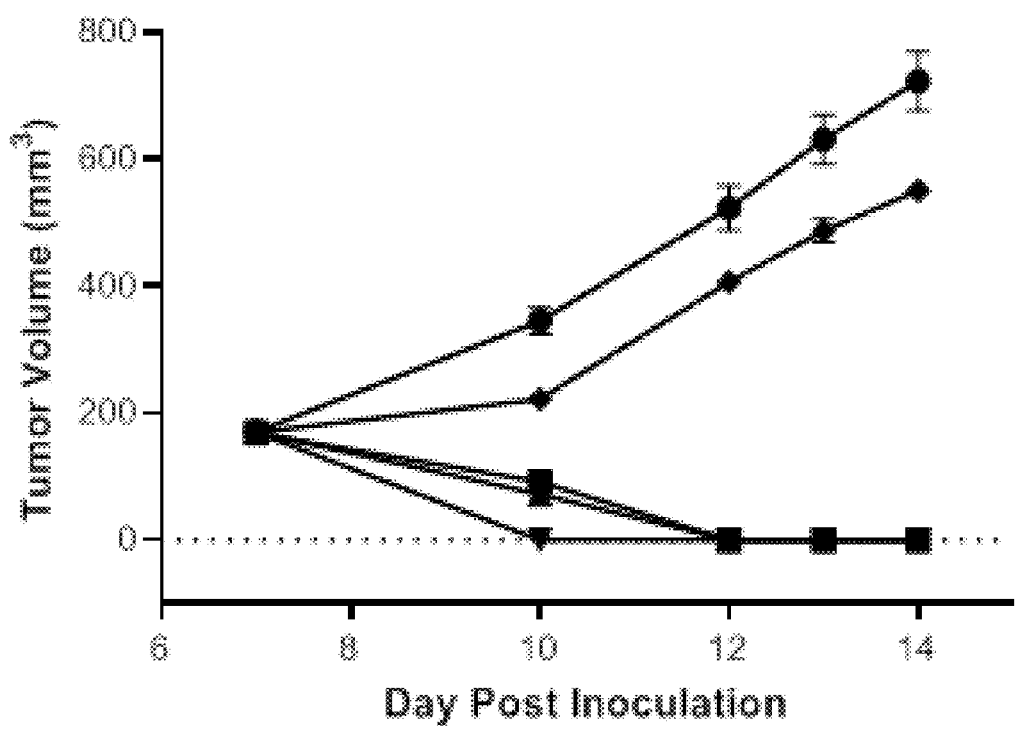
FIG. 2A shows tumor volumes of xenograft tumor models in mice bearing Ba/F3 cell derived xenograft tumors harboring an EML4-ALK fusion with a L1198F/G1202R mutation. (●) vehicle; (■) Compound 1 (2 mg/kg BID); (▲) Compound 1 (5 mg/kg BID); (▼) Compound 1 (10 mg/kg BID); (♦) Lorlatinib (5 mg/kg).

Effect of Compound 1 on Ba/F3 Cell-Derived Xenograft Tumors with the EML4-ALK L1198F/G1202R Fusion SCID/Beige mice bearing Ba/F3 cell-derived tumors with the EML4-ALK L1198F/G1202R fusion were randomized to five groups with 10 mice per group on day 7 post inoculation and treated with vehicle BID, Compound 1 BID at 2 mg/kg, Compound 1 BID at 5 mg/kg, Compound 1 BID at 10 mg/kg, and lorlatinib BID at 5 mg/kg, respectively. The tumor volume vs time data are shown as mean±sem in FIG. 2A. After 7 days of treatment, Compound 1 treatment led to complete tumor regression with TGIs of 200% at all three dose levels of 2, 5, and 10 mg/kg BID. Tumors in all three groups treated with Compound 1 exhibited complete regression at the end of study on day 14 post inoculation. The inhibitory activity of Compound 1 in this model with the EML4-ALK L1198F/G1202R fusion was much better than that of lorlatinib, which inhibited tumor growth to a much less extent with a TGI of 31% at 5 mg/kg BID after 7 days of treatment. The statistical evaluation of Compound 1's effect on tumor volume was performed using two-way repeated measures ANOVA followed by post hoc Tukey's multiple comparisons test. The tumor volume in the group treated with Compound 1 at all three dose levels was significantly smaller than that of the group treated with vehicle on days 10, 12, 13, 14 post inoculation (p<0.0001 for Compound 1 2, 5, or 10 mg/kg vs vehicle on either day 10, 12, 13 or 14). Furthermore, the tumor volume in the group treated with Compound 1 at all three dose levels was significantly smaller than that of the group treated with lorlatinib on days 10, 12, 13, 14 post inoculation (p<0.0001 for Compound 1 2, 5, or 10 mg/kg vs lorlatinib on either day 10, 12, 13 or 14).

Figure 2B:
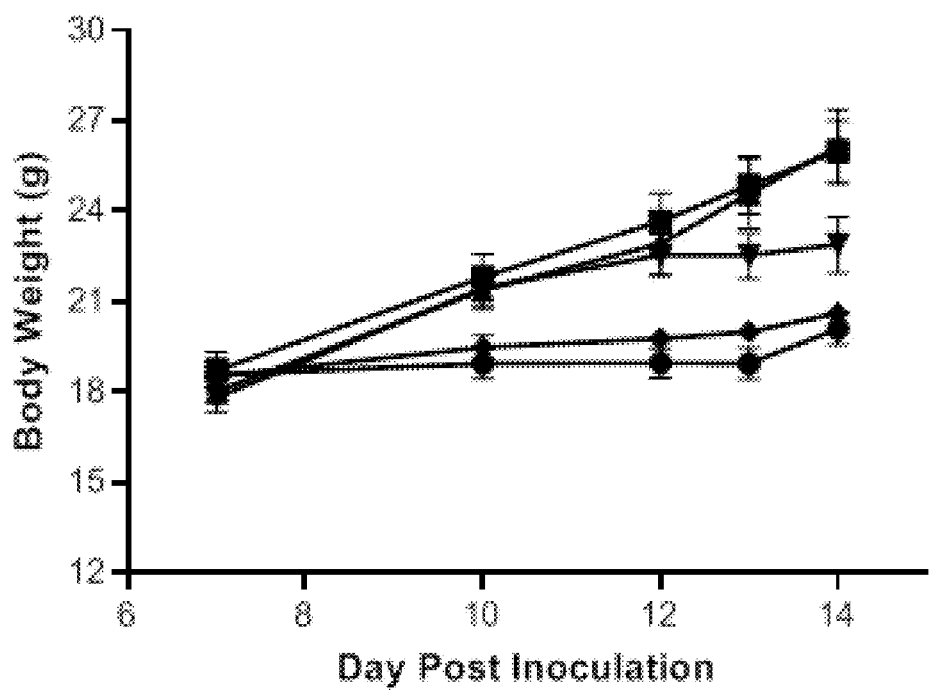
FIG. 2B shows body weights of mice bearing Ba/F3 cell derived xenograft tumors harboring an EML4-ALK fusion with a L1198F/G1202R mutation. (●) vehicle; (■) Compound 1 (2 mg/kg BID); (▲) Compound 1 (5 mg/kg BID); (▼) Compound 1 (10 mg/kg BID); (♦) Lorlatinib (5 mg/kg).

The body weight vs time data are shown as mean±sem in FIG. 2B. There was no body weight loss in groups treated with Compound 1 at 2, 5, 10 mg/kg BID after 7 days of treatment. The statistical evaluation of Compound 1's effect on body weight was performed using two-way repeated measures ANOVA followed by post hoc Tukey's multiple comparisons test. The body weight in the group treated with Compound 1 at 2 mg/kg BID was significantly higher than that of the group treated with vehicle on days 10, 12, 13, 14 post inoculation (p=0.0478 on day 10, p=0.0044 on day 12, p=0.0008 on day 13, p=0.0013 on day 14). The body weight in the group treated with Compound 1 at 5 mg/kg BID was significantly higher than that of the group treated with vehicle on days 12, 13, 14 post inoculation (p=0.0308 on day 12, p=0.0056 on day 13, p=0.0050 on day 14). The body weight in the group treated with Compound 1 at 10 mg/kg BID was significantly higher than that of the group treated with vehicle on days 10, 12, 13 post inoculation (p=0.0390 on day 10, p=0.0048 on day 12, p=0.0119 on day 13).

Figure 3A:
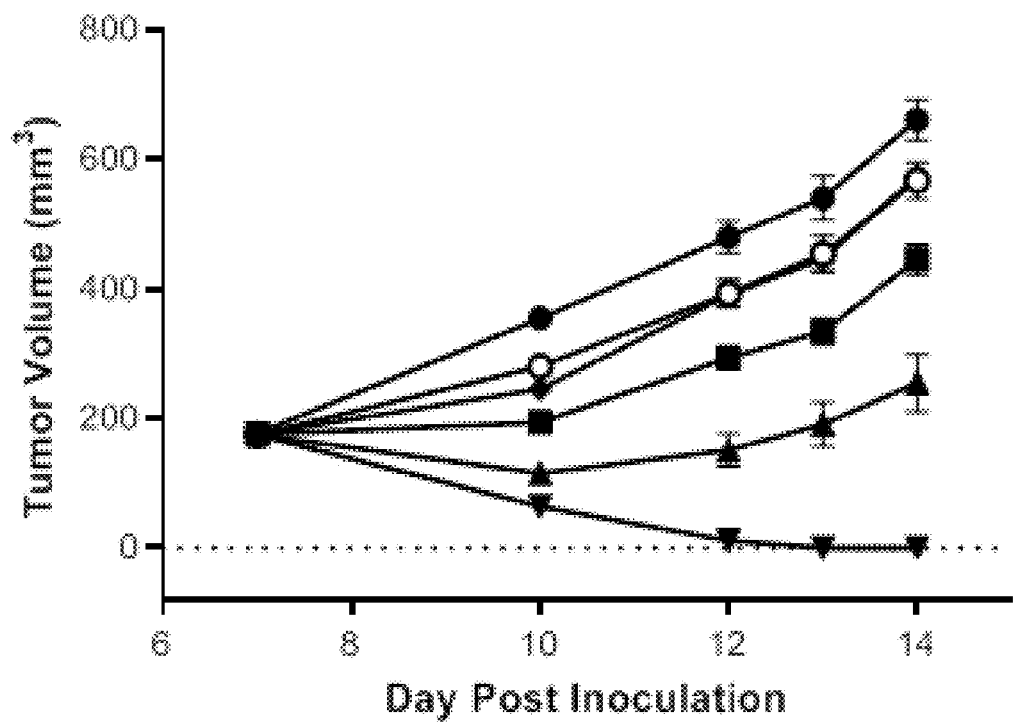
FIG. 3A shows tumor volumes of xenograft tumor models in mice bearing Ba/F3 cell derived xenograft tumors harboring an EML4-ALK fusion with a L1196M/G1202R mutation. (●) vehicle; (○) Compound 1 (0.6 mg/kg BID); (⌡) Compound 1 (2 mg/kg BID); (▲) Compound 1 (5 mg/kg BID); (▼) Compound 1 (10 mg/kg BID); (♦) Lorlatinib (5 mg/kg).

Effect of Compound 1 on Ba/F3 Cell-Derived Xenograft Tumors with the EML4-ALK L1196M/G1202R Fusion SCID/Beige mice bearing Ba/F3 cell-derived tumors with the EML4-ALK L1196M/G1202R fusion were randomized to six groups with 8 mice per group on day 7 post inoculation and treated with vehicle BID, Compound 1 BID at 0.6 mg/kg, Compound 1 BID at 2 mg/kg, Compound 1 BID at 5 mg/kg, Compound 1 BID at 10 mg/kg, and lorlatinib BID at 5 mg/kg, respectively. The tumor volume vs time data are shown as mean±sem in FIG. 3A. After 7 days of treatment, Compound 1 treatment resulted in TGIs of 19%, 44%, 83% and 200% at dose levels of 0.6, 2, 5, and 10 mg/kg BID, respectively; whereas lorlatinib inhibited tumor growth with a TGI of 18% at 5 mg/kg BID after 7 days of treatment. The statistical evaluation of Compound 1's effect on tumor volume was performed using mixed-effects model followed by post hoc Tukey's multiple comparisons test. The tumor growth in the groups treated with Compound 1 at 0.6 mg/kg BID or lorlatinib at 5 mg/kg BID was not significantly different from vehicle treated group after 7 days of treatment (p>0.05 for vehicle vs lorlatinib or Compound 1 0.6 mg/kg on day 14). Compound 1 at 2, 5 and 10 mg/kg BID exhibited effectiveness in this model with the EML4-ALK L1196M/G1202R fusion. After seven days of treatment, the tumor volume in the group treated with Compound 1 at 2, 5 or 10 mg/kg BID was significantly smaller than that of the group treated with vehicle (on day 14, p=0.0013 for Compound 1 2 mg/kg vs vehicle, p=0.0001 for Compound 1 5 mg/kg vs vehicle, p<0.0001 for Compound 1 10 mg/kg vs vehicle). Moreover, after seven days of treatment, the tumor volume in the group treated with Compound 1 at 2, 5 or 10 mg/kg BID was significantly smaller than that of the group treated with lorlatinib (on day 14, p=0.0070 for Compound 1 2 mg/kg vs lorlatinib, p=0.0018 for Compound 1 5 mg/kg vs lorlatinib, p<0.0001 for Compound 1 10 mg/kg vs lorlatinib).

Figure 3B:
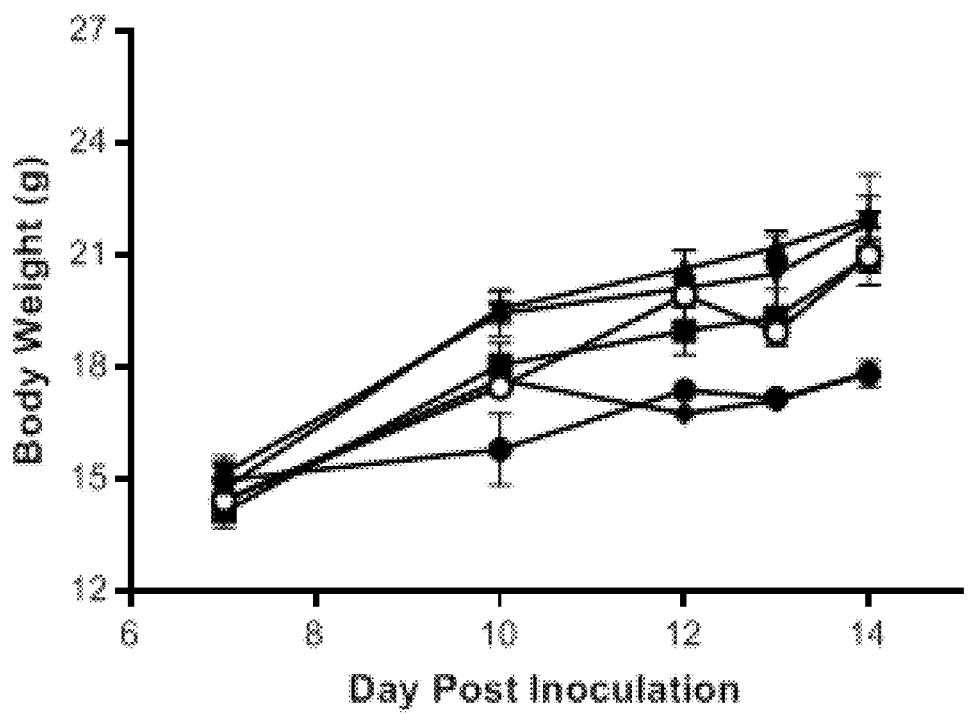
FIG. 3B shows body weights of mice bearing Ba/F3 cell derived xenograft tumors harboring an EML4-ALK fusion with a L1196M/G1202R mutation. (●) vehicle; (○) Compound 1 (0.6 mg/kg BID); (■) Compound 1 (2 mg/kg BID); (▲) Compound 1 (5 mg/kg BID); (▼) Compound 1 (10 mg/kg BID); (♦) Lorlatinib (5 mg/kg).

The body weight vs time data are shown as mean±sem in FIG. 3B. There was no body weight loss in groups treated with Compound 1 at 2, 5, 10 mg/kg BID after 7 days of treatment. The statistical evaluation of Compound 1's effect on body weight was performed using mixed-effects model followed by post hoc Tukey's multiple comparisons test. The body weight in the group treated with Compound 1 at 0.6 mg/kg BID was significantly higher than that of the group treated with vehicle on days 12, 13, 14 post inoculation (p=0.0005 on day 12, p=0.0163 on day 13, p=0.0011 on day 14). The body weight in the group treated with Compound 1 at 2 mg/kg BID was significantly higher than that of the group treated with vehicle on day 14 post inoculation (p=0.0391 on day 14). The body weight in the group treated with Compound 1 at 5 mg/kg BID was significantly higher than that of the group treated with vehicle on days 10, 12, 13, 14 post inoculation (p=0.0413 on day 10, p=0.0018 on day 12, p<0.0001 on day 13, p=0.0011 on day 14). The body weight in the group treated with Compound 1 at 10 mg/kg BID was not significantly different from that of the group treated with vehicle (p>0.05 on day 10, 12, 13 and 14).

Figure 4:
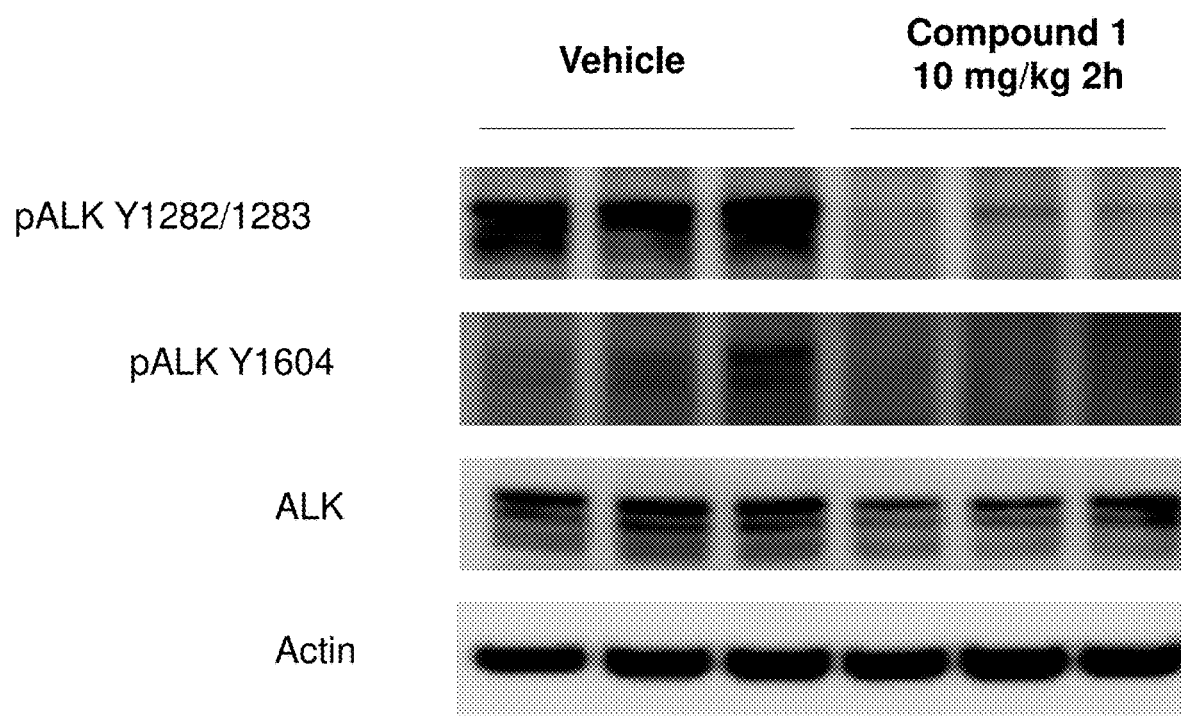
FIG. 4 shows the inhibition of phosphorylation of ALK fusions at Y1282/1283 and at Y1604, and reduction in the level of ALK fusion expression in mice treated with Compound 1 at 10 mg/kg BID. As the control, the expression level of actin was not affected by Compound 1 treatment.

Effect of Compound 1 on Phosphorylation of ALK Fusion Protein in Ba/F3 Cell-Derived Xenograft Tumors with the EML4-ALK L1196M/G1202R Fusion The pharmacodynamic effect of Compound 1 was evaluated in the Ba/F3 cell-derived xenograft tumors with the EML4-ALK L1196M/G1202R fusion following a single oral dose of Compound 1 at 10 mg/kg. At 2 hours post dose, tumor samples were collected from mice treated with either vehicle or Compound 1 with three mice for each treatment. Samples were processed and analyzed by immunoblotting and the result is shown in FIG. 4. The levels of phosphorylation of ALK fusions at Y1282/1283 and at Y1604 were both reduced in samples from the Compound 1 treated mice compared to those from vehicle treated mice. The level of ALK fusion expression was also reduced in the samples from Compound 1 treated mice compared to those from vehicle treated mice. As the control, the expression level of actin was not affected by Compound 1 treatment.

Figure 5:
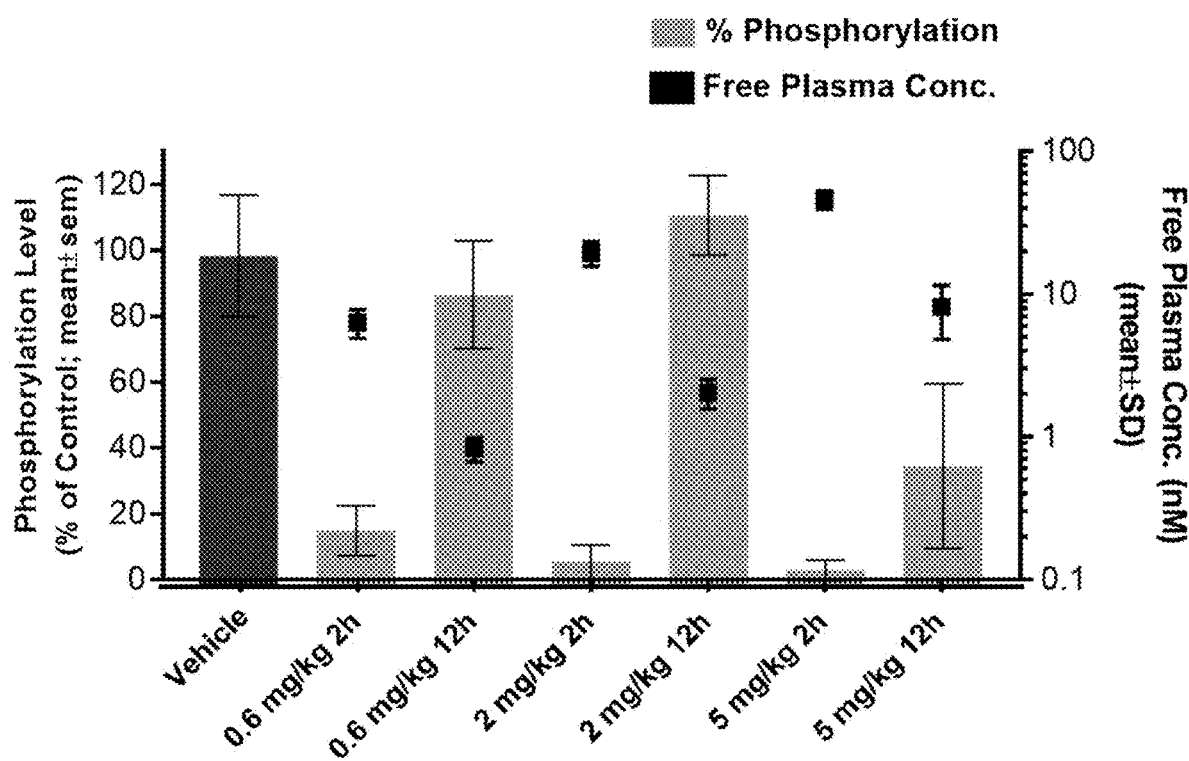
FIG. 5 shows the inhibition of phosphorylation of ALK fusions as a function of free plasma concentration of compound upon dosing of Compound 1 at 0.6, 2, or 5 mg/kg after 2 hours or 12 hours in mice bearing Ba/F3 cell derived xenograft tumors harboring an EML4-ALK fusion with a L1196M/G1202R mutation.

FIG. 5 shows ALK phosphorylation level post-in vivo dosing of Compound 1 at 0.6, 2, or 5 mg/kg after 2 hours or 12 hours. At each dose, phosphorylation level was significantly reduced compared to control at 2 hours, but only showed reduction at 12 hours at the highest dose.

The invention claimed is:

1. A compound having structure:

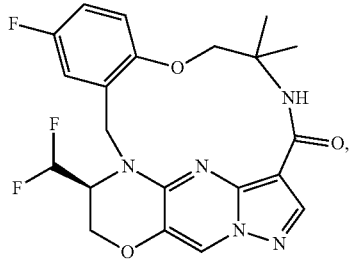 [SMILES: CC1(C)COc2ccc(F)cc2CN2c3nc4c(cnn4cc3OC[C@H]2C(F)F)C(=O)N1]

or a pharmaceutically acceptable salt thereof.

2. A compound having structure:

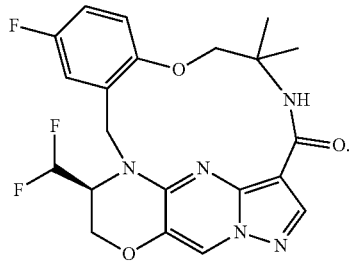 [SMILES: CC1(C)COc2ccc(F)cc2CN2c3nc4c(cnn4cc3OC[C@H]2C(F)F)C(=O)N1]

3. A pharmaceutical composition comprising a compound having structure:

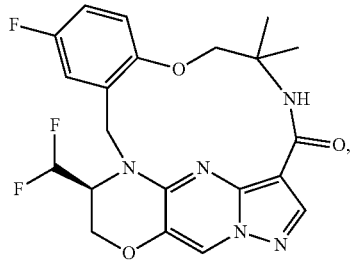 [SMILES: CC1(C)COc2ccc(F)cc2CN2c3nc4c(cnn4cc3OC[C@H]2C(F)F)C(=O)N1]

or a pharmaceutically acceptable salt thereof, and a pharmaceutically acceptable diluent, carrier or excipient.

* * * * *

UNITED STATES PATENT AND TRADEMARK OFFICE
CERTIFICATE OF CORRECTION

PATENT NO. : 11,142,533 B2  
APPLICATION NO. : 17/214096  
DATED : October 12, 2021  
INVENTOR(S) : Evan W. Rogers et al.

Page 1 of 1

It is certified that error appears in the above-identified patent and that said Letters Patent is hereby corrected as shown below:

In the Specification

At Column 48, Line Numbers 2-14, delete chemical structure " 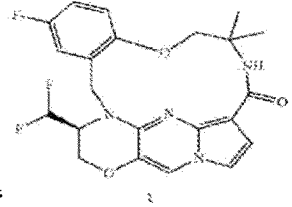 " and insert 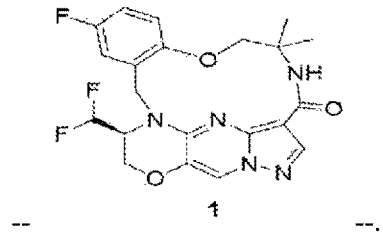 --.

Signed and Sealed this  
Second Day of August, 2022

Katherine Kelly Vidal  
*Director of the United States Patent and Trademark Office*